(12) United States Patent
Bedor

(10) Patent No.: US 12,611,231 B2
(45) Date of Patent: Apr. 28, 2026

(54) SPINAL ROD AND SYSTEMS THEREOF

(71) Applicant: SPINAL RESOURCES, INC., Fort Lauderdale, FL (US)

(72) Inventor: Bernard M. Bedor, Fort Lauderdale, FL (US)

(73) Assignee: Spinal Resources, Inc., Fort Lauderdale, FL (US)

( * ) Notice: Subject to any disclaimer, the term of this patent is extended or adjusted under 35 U.S.C. 154(b) by 185 days.

(21) Appl. No.: 18/532,262

(22) Filed: Dec. 7, 2023

(65) Prior Publication Data

US 2024/0325054 A1 Oct. 3, 2024

Related U.S. Application Data

(60) Provisional application No. 63/455,452, filed on Mar. 29, 2023.

(51) Int. Cl.
*A61B 17/70* (2006.01)
*A61B 17/00* (2006.01)

(52) U.S. Cl.
CPC ...... *A61B 17/7005* (2013.01); *A61B 17/7011* (2013.01); *A61B 17/7041* (2013.01); *A61B 2017/00526* (2013.01)

(58) Field of Classification Search
CPC ............ A61B 17/7004; A61B 17/7005; A61B 17/7011; A61B 17/7032; A61B 17/7041
See application file for complete search history.

(56) References Cited

U.S. PATENT DOCUMENTS

| | | | |
|---|---|---|---|
| 443,764 | A | 12/1890 | Hilliard |
| 5,024,213 | A | 6/1991 | Asher et al. |
| 5,217,461 | A | 6/1993 | Asher et al. |
| 5,593,408 | A | 1/1997 | Gaynet et al. |
| 5,601,554 | A | 2/1997 | Howland et al. |
| 6,102,912 | A | 8/2000 | Cazin et al. |
| 6,547,790 | B2 | 4/2003 | Harkey, III et al. |
| 7,794,476 | B2 | 9/2010 | Wisnewski |

(Continued)

FOREIGN PATENT DOCUMENTS

CA 3116288 A1 4/2020

OTHER PUBLICATIONS

Definition of "Method", Dictionary [online], Merriam-Webster, 2025. Retrieved from the Internet: <URL:https://www.merriam-webster.com/dictionary/method>, 10 pages.

(Continued)

*Primary Examiner* — Eduardo C Robert
*Assistant Examiner* — Holly Joanna Lane
(74) *Attorney, Agent, or Firm* — McDonald Hopkins LLC

(57) ABSTRACT

A spinal rod may comprise at least two segments having a constant diameter, where a first segment has a first constant diameter and a second segment has a second constant diameter, and where the first constant diameter is different from the second constant diameter. The spinal rod may also comprise a transition region positioned between the at least two segments, where the transition region has a variable diameter that gradually transitions between the first constant diameter and the second constant diameter, where the transition region comprises a tapered shape, and at least one curve extending along the at least two segments.

18 Claims, 19 Drawing Sheets

(56) References Cited

U.S. PATENT DOCUMENTS

| | | | |
|---|---|---|---|
| 7,806,913 | B2 | 10/2010 | Fanger et al. |
| 7,875,059 | B2 | 1/2011 | Patterson et al. |
| 7,967,847 | B2 | 6/2011 | Barker, Jr. et al. |
| 8,236,035 | B1 | 8/2012 | Bedor |
| 8,641,735 | B2* | 2/2014 | Serbousek ......... A61B 17/7004 |
| | | | 606/259 |
| 8,657,856 | B2 | 2/2014 | Gephart et al. |
| 8,771,318 | B2 | 7/2014 | Triplett et al. |
| 9,289,243 | B2 | 3/2016 | Dekutoski et al. |
| 10,588,642 | B2 | 3/2020 | Gauthier et al. |
| 10,758,274 | B1 | 9/2020 | Bess et al. |
| 11,160,583 | B2* | 11/2021 | Lee .................... A61B 17/7032 |
| 2003/0060824 | A1 | 3/2003 | Viart et al. |
| 2003/0191470 | A1 | 10/2003 | Ritland |
| 2005/0085815 | A1 | 4/2005 | Harms et al. |
| 2007/0049937 | A1 | 3/2007 | Matthis et al. |
| 2007/0191841 | A1 | 8/2007 | Justis et al. |
| 2007/0276380 | A1 | 11/2007 | Jahng et al. |
| 2009/0204156 | A1 | 8/2009 | McClintock et al. |
| 2010/0094302 | A1 | 4/2010 | Pool et al. |
| 2010/0114165 | A1* | 5/2010 | Ely .................... A61B 17/7004 |
| | | | 606/264 |
| 2010/0114167 | A1 | 5/2010 | Wilcox et al. |
| 2012/0065687 | A1* | 3/2012 | Ballard .............. A61B 17/7031 |
| | | | 606/279 |
| 2012/0071928 | A1 | 3/2012 | Jackson |
| 2012/0116458 | A1 | 5/2012 | Van Nortwick et al. |
| 2012/0290013 | A1* | 11/2012 | Simonson .......... A61B 17/7004 |
| | | | 606/279 |
| 2013/0158606 | A1 | 6/2013 | Freudiger et al. |
| 2014/0236239 | A1 | 8/2014 | Biedermann et al. |
| 2014/0257393 | A1* | 9/2014 | Trieu ................. A61B 17/7004 |
| | | | 606/279 |
| 2014/0316420 | A1 | 10/2014 | Ballard et al. |
| 2015/0157363 | A1 | 6/2015 | Noordeen et al. |
| 2015/0282842 | A1 | 10/2015 | Beyar et al. |
| 2016/0106471 | A1 | 4/2016 | Lynch et al. |
| 2017/0281237 | A1 | 10/2017 | Murray et al. |
| 2018/0168694 | A1 | 6/2018 | Lee et al. |
| 2019/0269438 | A1 | 9/2019 | Simpson et al. |
| 2019/0374257 | A1* | 12/2019 | Bedor ................ A61B 17/7005 |
| 2020/0315708 | A1* | 10/2020 | Mosnier ................. G16H 50/20 |
| 2024/0260994 | A1* | 8/2024 | Seiler ................... A61B 17/701 |

OTHER PUBLICATIONS

Hu et al. "Vertebral column decancellation in Pott's deformity: use of Surgimap Spine for preoperative surgical planning, retrospective review of 18 patients." BMC Musculoskeletal Disorders 19 (2018): 1-9.

Office Action in U.S. Appl. No. 19/085,445, mailed Jun. 5, 2025, 24 pages.

Parmar, A., "With AI, 3D imaging and a robot, Medtronic Spine aims to leave competitors bent out of shape," MedCity News, Dec. 15, 2020. Retrieved from the Internet: <URL:https://medcitynews.com/2020/12/with-ai-3d-imaging-and-a-robot-medtronic-spine-aims-to-leave-competitors-bent-out-of-shape/>, 12 pages.

SpineShape. The dynamic solution for your back. Technical information to System IV, Datasheet [online], 2020. Retrieved from the Internet: <URL:https://pdf.medicalexpo.com/pdf/spinesave/spineshape/4580159-269407-_12.html>, 9 pages.

Office Action in U.S. Appl. No. 19/085,445, mailed Jan. 14, 2026, 69 pages.

* cited by examiner

100

124

127

2
[.079]

124

100

SRI   LLMM
RSSC47-LL
WPG LOT NO.

127

100

116

112

100

114

400

410

Surgical
Planning

420

Osteotomy
Simulation

430

260

AI Optimized
Patient Specific
Multi-Diameter Rods

SPINAL ROD AND SYSTEMS THEREOF

CROSS REFERENCE TO RELATED APPLICATIONS

The application claims priority to U.S. Patent Application No. 63/455,452, filed on Mar. 29, 2023, entitled "SPINAL ROD AND SYSTEMS THEREOF," which is incorporated herein by reference in its entirety.

FIELD OF THE INVENTION

The present disclosure relates generally to implantable systems and spinal rods including elongated structures with regions having different rigidity and, more specifically, to stabilization systems that use one or more fixation rods for placement by a patient's spinal column with gradual transitions between regions having a different cross-sectional dimension, where the fixation rods are adaptable to the custom morphology of a patient, and methods of use thereof.

BACKGROUND

Conventional stabilization systems include rods that, when installed, stabilize and fix a spinal segment to treat various spinal conditions. The rods have a constant cross-sectional area along their entire length, and are chosen based on the cross-sectional area to provide the rigidity warranted by a specific application. However, the constant cross-sectional area of each rod constrains the surgeon during surgery by requiring the same cross-sectional area, and accordingly, the same rod stiffness or rigidity to be placed along the entire spinal segment to be stabilized. Additionally, maximizing fixation rod stiffness can potentially lead to stress shielding, implant loosening, proximal junction kyphosis or failure (PJK/PJF), and/or implant failure.

Attempts have been made to develop a stabilizing system with rods of different cross-sectional areas. Such systems can employ multiple different rods coupled together in a linear arrangement. Each different rod can have a cross-sectional area along its entire length, chosen to support the specific spinal segment of interest. However, such stabilizing systems require the different rods to be manually coupled together with couplers or brackets. The use of such connecting structures introduces locations where the connection can weaken due to fatigue over time, requiring surgical intervention to correct. Further, the location of the fastener coupling the separate rods together must be taken into consideration when implanting the stabilizing system, and may interfere with placement of the stabilizing system.

To attempt to mitigate implant loosening, adjacent segment degeneration, and PJK/PJF, a number of different semi-rigid and/or mobile devices have been developed, but have limitations. One such proximal fixation method includes posterior spinal fixation rods that are augmented with discrete stepped reductions in outer diameter, see FIG. 5, for example, also showing a rod having a constant diameter compared with rod 100 of the present disclosure. The decreased proximal stiffness of the stepped rods could allow for a more gradual transfer of loads from the implant to the screw-bone interface and to the adjacent proximal segment, potentially reducing stress shielding and thereby mitigating the propensity for implant loosening.

However, despite these potential benefits of a stepped rod, the current stepped diameter fixation rods are subject to a number of surgical and biomechanical limitations so that the benefits of the stepped rod cannot be fully realized. In both unilateral and bilateral spinal fixation rod implantation, screw placement presents a challenge. Screw placement is often determined by pedicle location in the vertebral body. For example, the distance to the adjacent screw is determined by the height of the adjacent body and the intervertebral disc and or interbody cage. The current stepped transition rods, however, when placed, must therefore be positioned such that the rod's transition junction (i.e. where the diameter steps down) is not above a pedicle screw head. Furthermore, the rod must be positioned in a way allowing adequate room for compression of the screw heads when necessary. Screw heads must also not encroach upon the stepped transition. The requirement of placing screws along rods away from transitions introduces intra-operative variability and often results in non-ideal rod placement. Specifically, any benefits in spatially varying rod flexibly offered by stepped rods are undermined because the surgeon is forced to accommodate the step, rather than accommodating the patient's anatomy.

Accordingly, there is a need for a stabilizing system including a fixation rod for placement by a patient's spinal column having a plurality of regions with a variable bending stiffness based on local diameter and that can be used to accommodate different patient's anatomy by enabling placement of screws even at rod transitions. There is a need for improved spinal rods and spinal systems that provide one or more (or all) of the following: spinal rods having different cross-sectional diameters; spinal rods having different cross-sectional diameters without requiring coupling or brackets to realize the different cross-sectional diameter regions (e.g., spinal rods that instead have a monolithic form or a generally continuous or smooth surface along their length, such as along the entire length of the spinal rod); spinal rods that are not susceptible to stress shielding, implant loosening, proximal junction kyphosis or failure (PJK/PJF), adjacent segment disease, implant failure, and/or any effect where the next vertebral body is impacted from the unlocking forces due to construct stiffness; adaptable spinal rods that are adaptable to a patient's morphology; and the like.

SUMMARY

The following presents a summary of this disclosure to provide a basic understanding of some aspects. This summary is intended to neither identify key or critical elements nor define any limitations of embodiments or claims. This summary may provide a simplified overview of aspects that may be described in greater detail in other portions of this disclosure. Any of the described aspects may be isolated or combined with other described aspects without limitation.

Provided is an implantable, elongated fixation rod that, when coupled to a spinal column in a patient, stabilizes a portion of the spinal column. In an embodiment, the elongated fixation rod includes a plurality of different rod regions that are aligned along a longitudinal axis of the elongated fixation rod. The elongated fixation rod may be formed as a single or continuous rod structure. The different rod regions can include different dimensions tailored to provide the different rigidities specific to the support needed at corresponding regions of the spinal column where the elongated fixation rod is to be installed. In an embodiment, a smooth transition region is integrally formed as part of a common monolithic structure with the different rod regions and separates the different rod regions along the longitudinal axis of the fixation rod. In an embodiment, the smooth transition region is further devoid of a full, sharp step that forms a 90° angle relative to the longitudinal axis of the elongated fixation rod.

Although embodiments herein may describe smooth transition regions having a length of approximately 5 mm, it is noted that the smooth transition regions may also have smaller and longer lengths without departing from this disclosure. For example, the smooth transition region may have a length of 0.01 mm up to 10, 20, 30, 40 mm, including all values therebetween. It is noted that anything smaller than the smooth transition region as herein described would instead be a stepped region. Generally, instead of a stepped region, the smooth transition region may be further understood and described as a gradual transition connecting two regions having different diameters. In an embodiment, the smooth transition region may allow for proper anterior bending and rotation, and can enable placement of a transition segment within a linear segment (as well as but not limited to, between two linear segments), further allowing for the control of kick and flex points on the elongated fixation rod. The transition region may comprise a tapered shape. In some embodiments, the transition region may gradually taper.

In an embodiment, the elongated fixation rod for placement by a patient's spinal column comprises a plurality of regions with a variable bending stiffness based on local diameter and can be used to accommodate different patient's anatomy by enabling placement of screws even at rod transitions. The improved spinal rods and spinal systems can provide one or more (or all) of the following: spinal rods having different cross-sectional diameters; spinal rods having different cross-sectional diameters without requiring coupling or brackets to realize the different cross-sectional diameter regions (e.g., spinal rods that instead have a monolithic form or a generally continuous or smooth surface along their length); spinal rods that are not susceptible to stress shielding, implant loosening, proximal junction kyphosis or failure (PJK/PJF), adjacent segment disease, implant failure, and/or any effect where the next vertebral body is impacted from the unlocking forces due to construct stiffness; adaptable spinal rods that are adaptable to a patient's morphology; and the like.

A spinal rod may comprise at least two segments having a constant diameter, where a first segment has a first constant diameter and a second segment has a second constant diameter, and where the first constant diameter is different from the second constant diameter. The spinal rod may also comprise a transition region positioned between the at least two segments, where the transition region has a variable diameter that gradually transitions between the first constant diameter and the second constant diameter, where the transition region comprises a tapered shape, and at least one curve extending along the at least two segments.

The spinal rod may comprise any one of the following in any combination:

the at least two segments and the transition region are monolithically formed.

the at least two segments and the transition region are devoid of a full, sharp step that forms a 90° angle relative to a longitudinal axis of the at least two segments and the transition region.

the at least two segments and the transition region comprise a smooth surface across a full length thereof.

the transition region gradually tapers from the first constant diameter of the first segment to the second constant diameter of the second segment.

the transition region comprises a generally constant slope.

the transition region is at least 5 mm in length.

the at least one curve comprises a Bezier curve.

a third segment having a third constant diameter wherein the third constant diameter is different from the first and the second constant diameters and a second transition region between the second segment and the third segment.

a shape of the at least one curve is determined by an algorithm that determine common sets of morphologies based on a database of patient data.

a shape of the at least one curve and a length of each segment and transition region is customizable to a specific patient anatomy.

A fixation rod may comprise a first segment comprising a first constant diameter and a second segment comprising a second constant diameter, wherein the first constant diameter is different from the second constant diameter. The fixation rod may comprise a transition region positioned between the first and second segments, where the transition region has a variable diameter that gradually transitions between the first constant diameter and the second constant diameter and a curve in at least one of the first segment, the second segment and the transition region.

The spinal rod may comprise any one of the following in any combination:

the curve is in the first segment, the second segment and the transition region.

the first and second segments and the transition region are monolithically formed.

a longitudinal axis, wherein the first and second segments and the transition region are devoid of a step that forms a 90° angle relative to the longitudinal axis.

the first and second segments and the transition region form a smooth surface across a full length thereof.

the transition region gradually tapers from the first constant diameter of the first segment to the second constant diameter of the second segment.

the transition region has a constant slope.

the curve comprises is a Bezier curve.

a shape of the curve is determined by an algorithm that determines common sets of morphologies based on a database of patient data.

the curve and a length of the first and second segments and the transition region is customizable to a specific patient anatomy.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

BRIEF DESCRIPTION OF THE DRAWINGS

The invention may take physical form in certain parts and arrangement of parts, embodiments of which will be described in detail in this specification and illustrated in the accompanying drawings which form a part hereof and wherein.

Figure 1:
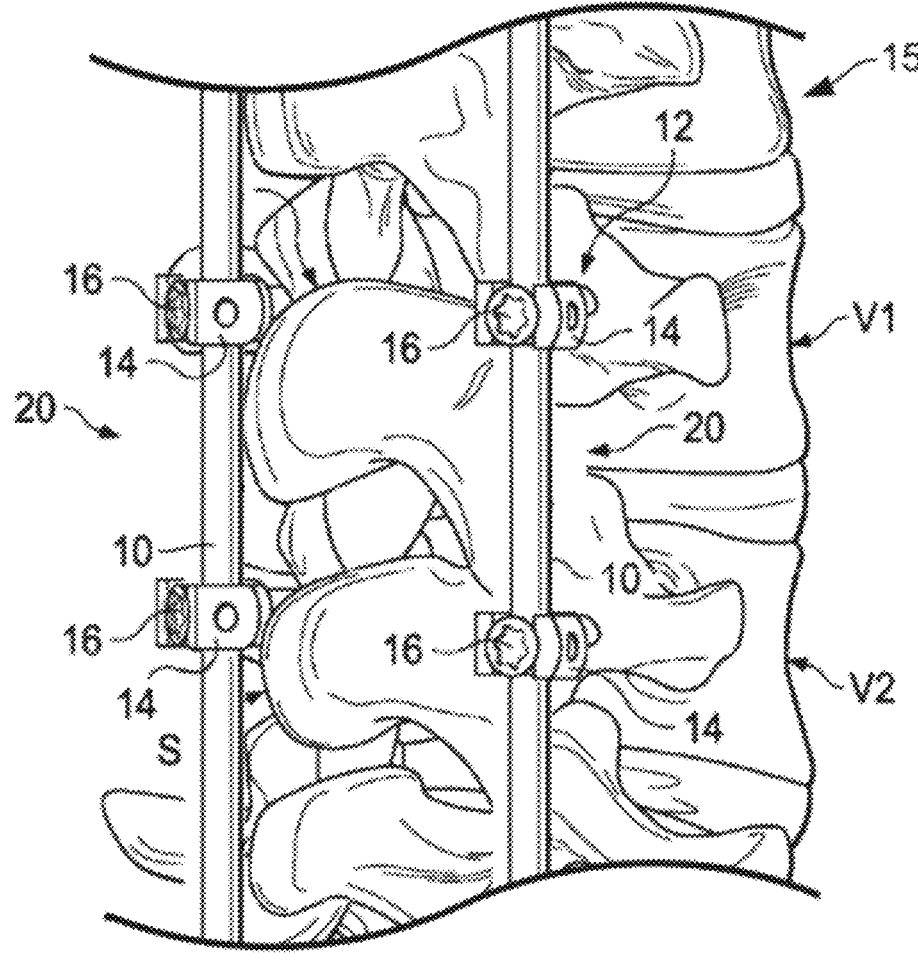
FIG. 1 is a perspective view of first and second stabilizing assemblies, each comprising a fixation rod having a plurality of regions with a different cross-sectional dimension attached to vertebral members according to one or more embodiments.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DETAILED DESCRIPTION

Reference will now be made in detail to exemplary embodiments of the present teachings, examples of which are illustrated in the accompanying drawings. It is to be understood that other embodiments may be utilized and structural and functional changes may be made without departing from the respective scope of the present teachings. Moreover, features of the various embodiments may be combined or altered without departing from the scope of the present teachings. As such, the following description is presented by way of illustration only and should not limit in any way the various alternatives and modifications that may be made to the illustrated embodiments and still be within the spirit and scope of the present teachings. In this disclosure, numerous specific details provide a thorough understanding of the subject disclosure. It should be understood that aspects of this disclosure may be practiced with other embodiments not necessarily including all aspects described herein, etc.

Certain terminology is used herein for convenience only and is not to be taken as a limitation on the present invention. Relative language used herein is best understood with reference to the drawings, in which like numerals are used to identify like or similar items. Further, in the drawings, certain features may be shown in somewhat schematic form.

As used herein, the words "example" and "exemplary" means an instance, or illustration. The words "example" or "exemplary" do not indicate a key or preferred aspect or embodiment. The word "or" is intended to be inclusive rather than exclusive, unless context suggests otherwise. As an example, the phrase "A employs B or C," includes any inclusive permutation (e.g., A employs B; A employs C; or A employs both B and C). As another matter, the articles "a" and "an" are generally intended to mean "one or more" unless context suggest otherwise.

It is also to be noted that the phrase "at least one of", if used herein, followed by a plurality of members herein means one of the members, or a combination of more than one of the members. For example, the phrase "at least one of a first widget and a second widget" means in the present application: the first widget, the second widget, or the first widget and the second widget. Likewise, "at least one of a first widget, a second widget and a third widget" means in the present application: the first widget, the second widget, the third widget, the first widget and the second widget, the first widget and the third widget, the second widget and the third widget, or the first widget and the second widget and the third widget.

Bone is a hard tissue that accumulates microscopic damage under conditions of normal physiological loading. This loading, in the form of walking down a flight of stairs, sneezing, bending over, etc. causes microscopic damage (microdamage). Unchecked, this microdamage is likely to accumulate over time. Fortunately, however, the body possesses the ability to repair microdamage through a process known as bone remodeling. Through this process, two types of cells remove damaged bone and replace it with new bone in a highly localized fashion (specifically, in the millimeter-scale region where microdamage is detected by the body). In addition to damage repair, the bone remodeling process also optimizes bone microarchitecture for maximum strength and minimum weight.

Bone cells also act to remove bone where no load is sensed in an effort to reduce overall weight of the bone. With the implantation of stiff metallic implants, which may be used in a variety of medical applications to address issues such as, but not limited to, undesired curvature of the spine, much of the load around the anchor points (often orthopedic screws) is sustained by the implant itself, rather than the bone. Consequently, bone tends to atrophy around the implant. This re-distribution of load away from the bone to the implant that results in bone atrophy is commonly referred to in the bone community as stress shielding.

Stress shielding is a concern because it induces local removal of bone directly around the anchor points (often orthopedic screws). The gap between the surrounding bone surfaces and the screw leads to micro-motion. Micro-motion can result in localized bone damage which further induces bone removal (i.e. as a damage repair process). Stress shielding thus causes increased loading in the implant itself, which can exceed design tolerances. This reduces the life of the implant and often results in premature clinical fatigue failure. Fatigue failure is that which results from many load-unload cycles over time at levels below the maximum load tolerance of the implant. Subsequent revision orthopedic surgery is then required to replace the implant. One approach to reducing stress shielding is to reduce load sustained by the implant by reducing its rigidity, allowing it to flex and accommodate micro-motion of the structure to which the implant is anchored. The present stabilization system and fixation rod 100 provides different, adequate anatomical support to separate regions of the patient, yet limits induction of bone atrophy. In an example, the smaller diameter portions of the stabilization system and fixation rod 100 as disclosed and described herein can be customized to match areas of weaker bone quality of a particular patient, which can reduce contact pressure, stress shielding, and micro motion that, in turn, creates increased pull out strength of the fasteners or screws (e.g., the fasteners or screws have a stronger placement, would require increased force to come out of place, and generally reduces strain on the patient's spine).

With the implantation of rigid external fixators where intermediate vertebrae are fused together, increased loading occurs under normal physiological loading post-surgery. The increased loading experienced by the top and bottom-most vertebrae is due to the increased stiffness provided by the fixator. Flexible fixation can help to mitigate the sudden change in stiffness that results in such clinical fractures. It is believed that there is an opportunity to reduce the prevalence of fractures by providing patients with external spine fixation that is optimally tuned (e.g., with compatible rigidity) to the local spinal anatomy. In an example, a linear segment of the stabilization system and fixation rod 100 can be lengthened, shortened, or otherwise modified in length to control or manipulate overall flex of the stabilization system and fixation rod 100. In an example, a transition segment of the stabilization system and fixation rod 100 can be lengthened, shortened, or otherwise modified in length to control or manipulate overall flex of the stabilization system and fixation rod 100. Alternatively or additionally, the positions of the linear segments and transition segments of the stabilization system and fixation rod 100 can also be used control or manipulate overall flex of the stabilization system and fixation rod 100. The positions of the linear segments and transition segments of the stabilization system and fixation rod 100 can further be located in strategic points above or below certain junctions to optimize biomechanically the reduction of construct stiffness. This type of customizable and precise flexibility optimization is not possible with a constant diameter, stepped, or conical rod. It is noted that although the term linear segment is used herein, the segment may also be referred to as a constant diameter segment and may be linear or may have a curvature as described herein.

Bone structure and spinal musculature vary along the vertebral column. The rigidity of the inventive stabilization system varies as well to accommodate the local, patient-specific, anatomical stiffness. Conventional fixation rods having a stepped design with linear regions having different diameters, however, can introduce highly localized stress concentrations. Stress concentrations exist because sharp features amplify local forces and can act as preferential sites of material failure, far below physiologically relevant loading. Stress concentrations in implanted devices reduce their life and can lead to premature failure.

Accordingly, embodiments of the present fixation rod 100 include smooth and/or gradual transition regions between each rod segment having different diameters, widths, heights, circumferences, perimeters, or other cross-sectional dimension. The transition regions can mitigate stress concentrations that would otherwise be present at the sharp steps (e.g., formed at 90° or other such angle), while providing the fixation rod 100 with continually variable stiffness along its length. The location and length of the transition regions as well as the variance in the diameters, widths, heights, circumferences, perimeters, or other cross-sectional dimension of the rod segments can be adapted to a specific patient's unique spinal morphology to further reduce stress concentrations and other disadvantages that are encountered with using conventional systems. Generally, the described systems and spinal rods may include transition zones to control the flexibility or rigidity of individual segments of a single spinal rod. Generally, the described systems and spinal rods may include longer or shorter segments (e.g., variability and control through length of the segments) to manipulate and control the flexibility at the apex (e.g., of a curve) based on the variable location of the transition zones on the rod. The described systems and spinal rods may be attached to the spine at any location to be stabilized, such as posterior, lateral, and anterior locations, for example. The described systems and spinal rods may also be attached at various sections of the spine, including the base of the skull and to vertebrae in the cervical, thoracic, lumbar, and sacral regions. The described systems and spinal rods may be used to provide alignment of the spine and/or to address deformities of the spine. In an embodiment, segmental alignment and/or segmental interventions may be used on spinal rods of any length. For example, the described systems and spinal rods can provide segmental customization, angles, curves, tapering, strengths, and flexibility that may be used to specifically adapt to a patient's individual anatomy. The precise tuning of alignment of the described systems and spinal rods can dramatically affect the efficacy and outcomes of the spinal rods, while minimizing contraindications. Even+/−1 degree, 5 degrees, and similar can lead to different alignment, efficacy, and outcomes of the spinal rods. In some embodiments, the transition region or regions may comprise a tapered shape.

Furthermore, reducing the outer diameter of the fixation rod 100, for example, can result in improved fatigue performance. In an embodiment, the outer diameter can be reduced 4.75 mm from 5.0 mm, to 5.0 mm from 5.5 mm, etc. It is noted that other starting and ending diameters and other amounts of reduction are also contemplated herein and form part of the disclosure. The values may be modified, for example, based on a patient's individual anatomy to provide custom morphology and desired rigidity or flexibility as described herein. For example, peak material stresses may occur at the outermost surfaces of a structure subjected to bending (such as that experienced during anterior or lateral bending of the spine). By reducing the diameter of the fixation rod 100 in regions of high bending, the peak material stresses are also reduced, resulting in improved fatigue life. Additionally, using more flexible instrumentation at the proximal segments may allow for a smoother transition from the highly rigid posterior fusion rods to the non-fused mobile proximal adjacent motion segments thereby providing a reduction in proximal junction angle, flexion force, moment, and lower intradiscal pressure. These and a gradual transfer of load to proximal segments may aid in reducing the risk of PJK/PJF. The described systems and spinal rods may further reduce or minimize adjacent segment disease and/or any effect where the next vertebral body is impacted from the unlocking forces due to construct stiffness.

With reference to the drawings, FIG. 1 shows first and second stabilization systems 20. Each stabilization system 20 includes a fixation rod 10 that has a plurality of linear regions D1, D2, see FIG. 2, with a different cross-sectional dimension attached to vertebral members V1, V2 by pedicle assemblies 12. Each pedicle assembly 12 includes a pedicle screw 14 and a retaining cap 16. To couple the fixation rod 10 to the vertebral members V1, V2, the pedicle screw 14 is threaded into an aperture formed in one of the vertebral members V1, V2. A saddle 17, shown in FIG. 2, of each pedicle assembly 12 receives a portion of the fixation rod 10. The saddle 17 can be formed as a generally U-shaped recess at a proximate end of the pedicle screw 14 that remains exposed externally of the bone while the pedicle screw 14 is installed in one of the vertebral members V1, V2. Threading 19 provided to a proximate end of the retaining cap 16 cooperates with threading 21 formed along an interior surface of the saddle 17 to exert a compressive force on the fixation rod 10, thereby securing the fixation rod 10 in the saddle 17.

The fixation rods 10 in FIG. 1 are positioned at a posterior side of the spine 15, on opposite sides of the spinous processes S. Fixation rods 10 may be attached to the spine 15 at any other location to be stabilized, such as lateral and anterior locations for example. The fixation rods 10 may also be attached at various sections of the spine, including the base of the skull and to vertebrae in the cervical, thoracic, lumbar, and sacral regions. Thus, the illustration in FIG. 1 is provided merely as a representative example of one application of a fixation rod 10.

In the exemplary assembly 20, the fixation rods 10 are secured to vertebral members V1, V2 by pedicle assemblies 12 comprising a pedicle screw 14 and a retaining cap 16. The outer surface of the fixation rod 10 is grasped, clamped, or otherwise secured between the pedicle screw 14 and retaining cap 16. In some embodiments, these are multi-axial or swedge pedicle screws, see FIG. 8, for example. Other mechanisms for securing fixation rods 10 to vertebral members V1, V2 include hooks, cables, and other such devices. Further, examples of other types of retaining hardware include threaded caps, screws, and pins. The fixation rods 10 may also be attached to plates in other configurations. In some examples, interbody devices or implants, fusion or dynamic, may be disposed between the adjacent vertebrae. Thus, the exemplary assemblies 20 shown in FIG. 1 are representative of one type of attachment mechanism and the disclosed systems and rods are not necessarily limited to these configurations and attachments.

Figure 2:
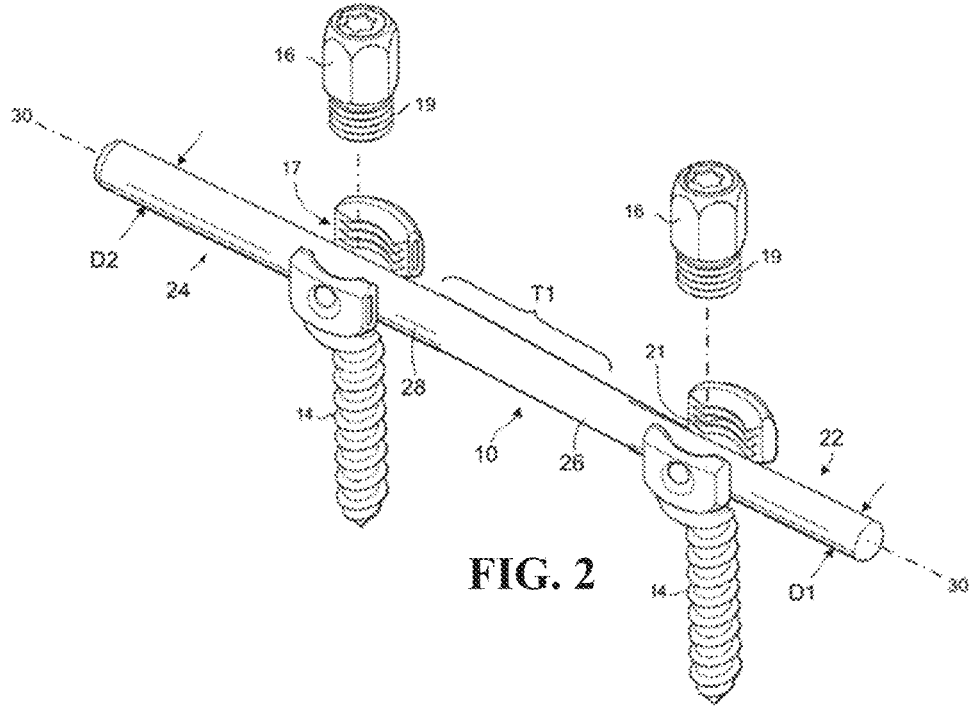
FIG. 2 is a perspective view of a fixation rod and a plurality of screws for anchoring a spinal implant to vertebral members.

As shown in FIG. 2, the fixation rod 10 includes a plurality of linearly-arranged rod regions 22, 24 separated by a transition region T1. The rod regions 21, 22 and the transition region T1 are integrally formed together as portions of the same monolithic structure, which can be substantially cylindrical in shape and have a generally circular or elliptical cross section, in an embodiment. Embodiments of the fixation rod 10 may be formed from surgical stainless steel, and can have any desired length to stabilize the region of the spine of interest. For example, the fixation rod 10 can have a length of up to 600 mm, up to 550 mm, up to 500 mm, up to 450 mm, up to 400 mm, up to 375 mm, up to 350 mm, etc. The fixation rod 10 is described herein as having a circular cross section for the sake of brevity and clarity, but other cross-sectional shapes can also be utilized to provide the fixation rod 10 with desired rigidity and other physical properties without departing from the scope of the present disclosure. The fixation rod 10 may also have different cross-sectional shapes at different points on the fixation rod 10, including in different rod regions 21, 22 or the transition region T1.

The circular cross section of the different regions 22, 24 can each have a different diameter D1, D2. The different diameters D1, D2 or circumferences (or other dimension of the rod regions 22, 24 if the cross section is not circular, such as width, height, perimeter, and the like) can be chosen to provide the respective regions with a desired rigidity to mitigate the effects of fatigue on the life of the implant due to movement of the respective spine segments. For example, the diameters D1, D2 can each be independently selected to be approximately 3.75 mm, 4.00 mm, 4.25 mm, 4.50 mm, 4.75 mm, 5.00 mm, 5.25 mm, 5.50 mm, 5.75 mm, any other diameter within a range from approximately 3.00 mm to about 6.00 mm, including any subrange therein. Examples of such subranges can be: up to 1.00 mm in size (e.g., D1 is approximately 4.50 mm and D2 is approximately 5.50 mm); up to 0.75 mm in size (e.g., D1 is approximately 4.50 mm and D2 is approximately 5.25 mm); up to 0.50 mm in size (e.g., D1 is approximately 4.50 mm and D2 is approximately 5.00 mm); etc. Having the approximate diameters above allows for machining tolerances of up to ±10%. In an example, the larger diameter sections (e.g., found at the distal end of the rod 10) can add support and the more narrow diameter sections (e.g., proximally), can add flexibility. It is noted that for any range described herein in this disclosure, the terms approximately or about are understood to include ±10% the described value.

Despite the different diameters D1, D2 of the different rod regions 22, 24, embodiments of the present stabilization system 20 can include same-sized pedicle assemblies 12, or portions thereof, to couple the fixation rod 10 to the vertebral members V1, V2. For example, pedicle screws 14 having a common saddle 17 size and common retaining cap 16 size can be installed along each of the rod regions 22, 24. Thus, the saddle 17 and retaining cap 16 can be sized to accommodate the largest of the diameters D1, D2, but create a range of adjustment that is suitable to allow the retaining cap 16 to secure the smallest of the diameters D1, D2 within the saddle 17. Pedicle assemblies 12 having different sizes may also be used to accommodate different sized rod regions 22, 24 of the fixation rod 10.

Forming different rod regions 22, 24 of the same fixation rod 10 with different diameters D1, D2 affords the different rod regions 22, 24 with different rigidity, tailored to the respective vertebral members V1, V2 to be stabilized by those rod regions 22, 24. To at least partially mitigate stress concentrations along the fixation rod 10, a transition region T1 forms a gradual transition between the different diameters D1, D2 of the rod regions 22, 24. Instead of a full and immediate step change in the diameter at a point location along the length of the fixation rod 10, the transition region T1 elongates the portion of the fixation rod 10 over which the diameter changes from the diameter D1 to the diameter D2. For example, a first end 26 of the transition region T1 can have a diameter that is approximately the same as diameter D1, while a second end 28 of the transition region T1 can have a diameter that is approximately the same as diameter D2. The first and second ends 26, 28 of the transition region T1 can be separated from each other by at least 5 mm, at least 10 mm, at least 15 mm, at least 20 mm, at least 25 mm, at least 30 mm, at least 35 mm, at least 40 mm, etc. along a longitudinal axis 30 of the fixation rod 10.

Embodiments of the transition region T1 can be limited in length along the longitudinal axis 30 to less than a defined threshold such as 50 mm, for example, to allow the individual rod regions 22, 24 to have a substantially cylindrical shape. Thus, fixation rod 10 can be formed from a plurality of cylindrical rod regions 22, 24, and a tapered transition region, optionally giving the fixation rod 10 a stepped shape instead of a conical shape, with continuous angled sides along the entire length of the fixation rod 10.

Figure 3:
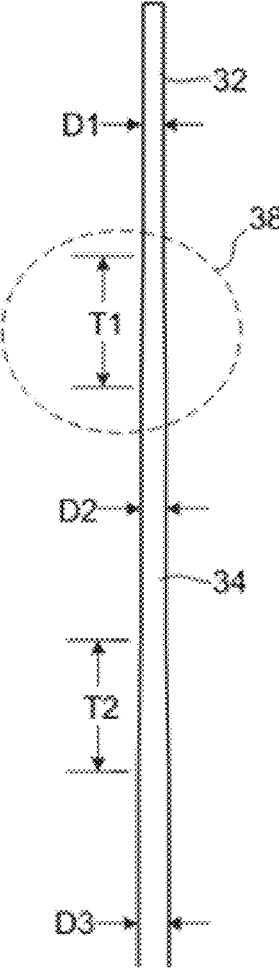
FIG. 3 is a top view of a fixation rod comprising three linear regions, each having a different diameter, and tapered transition regions separating the linear regions from each other.

The embodiment of the fixation rod 10 in FIG. 2 has two rod regions 22, 24 having different diameters D1, D2 separated by a transition region T1, however the present disclosure is not so limited. FIG. 3 shows another embodiment of the fixation rod 10 that includes three rod regions 32, 34, 36. Similar to the above embodiments, each rod region 32, 34, 36 can be cylindrical in shape with a substantially constant diameter D1, D2, D3 such as those described above. Transition regions T1, T2 separate the rod regions 32, 34, 36 from each other.

Figure 4:
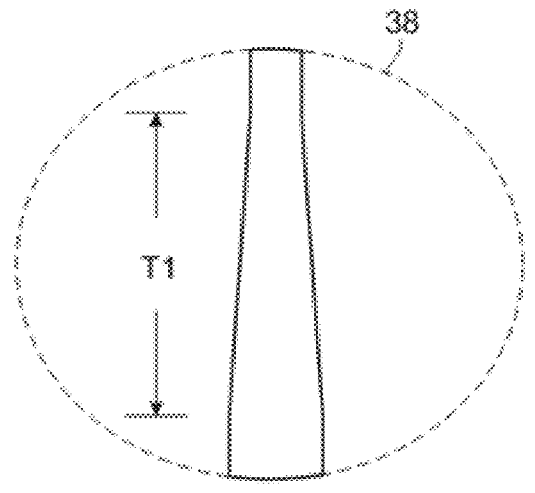
FIG. 4 is an enlarged view of the transition region encircled by broken lines in FIG. 3.
Figure 5:
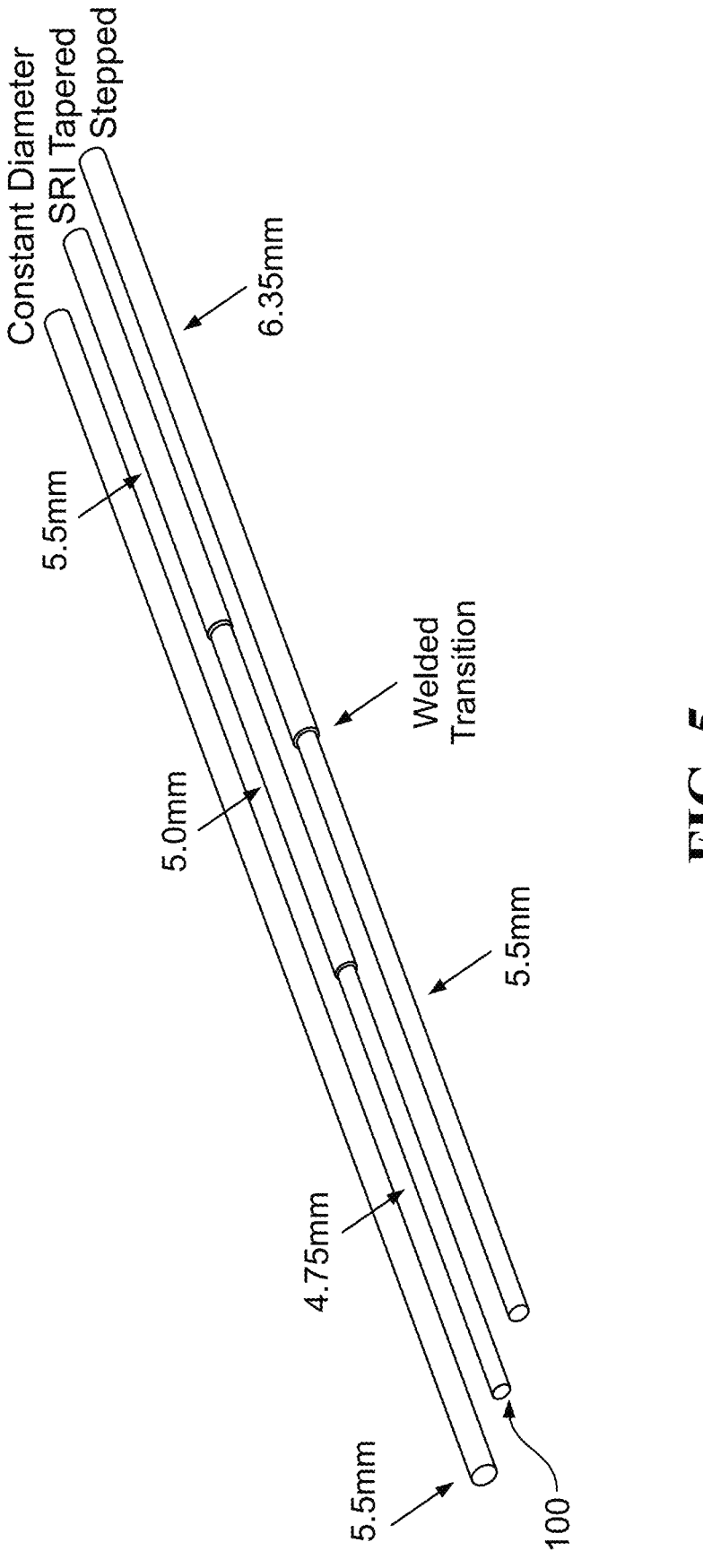
FIG. 5 shows embodiments of fixation rods having a tapered diameter compared to a conventional spinal rods having a constant diameter and having a stepped diameter.

Because the difference in diameter between rod regions 32, 34, 36 is subtle, FIG. 4 shows an enlarged view of the transition region T1 between the diameters D1, D2 enclosed by broken lines 38 in FIG. 3. The rate at which the diameter changes between diameters D1, D2 can optionally be constant across the length of the transition region T1. Thus, as shown in FIG. 4, the transition region T1 forms a substantially frusto-conical shape between the rod regions 32, 34. The transition region T1 affords surgeons the flexibility to install the pedicle assemblies 12 at any location along the length of the fixation rod 10, including along the transition region T1 or at an intersection of the transition region T1 and one of the rod regions 32, 34. The transition region T1, not having a step or large, immediate diameter change, such as that shown in FIG. 5 of the stepped rod, creating an obstacle or cantilever force when the locking cap touches the rod surface, allows compression and distraction of the rod without being restricted in the placement of the locking cap or the transition region relative the rod and spine.

Figure 6A:
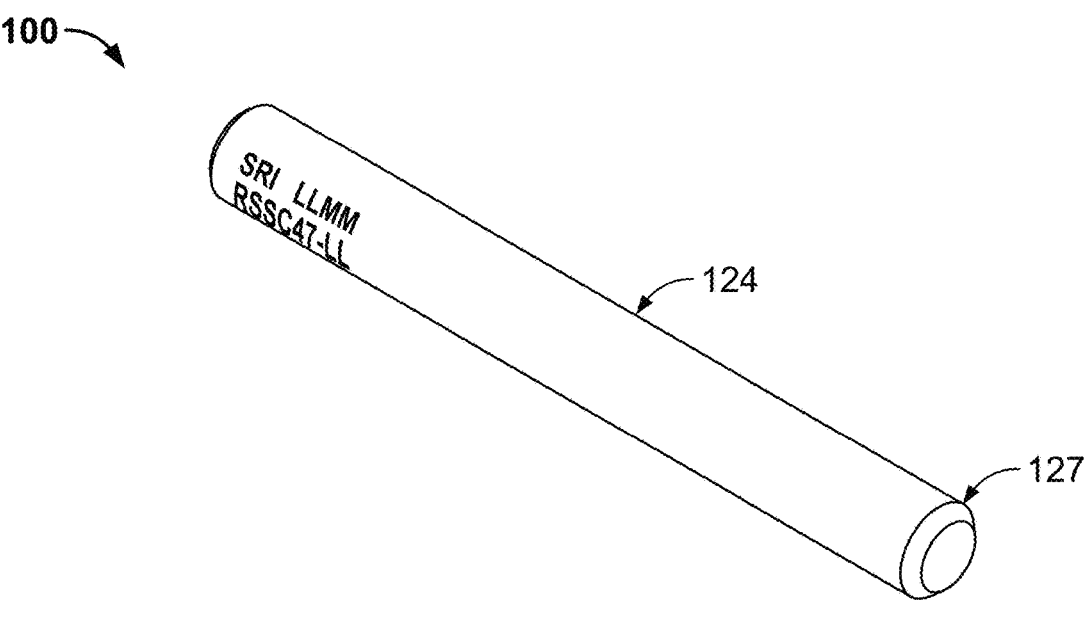
FIGS. 6A-C show various views of an embodiment of a fixation rod having a constant diameter and beveled edge in accordance with various disclosed aspects herein.
Figure 6B:
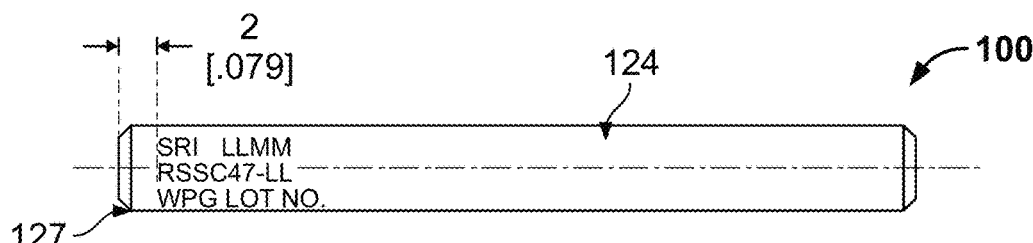
Figure 6C:
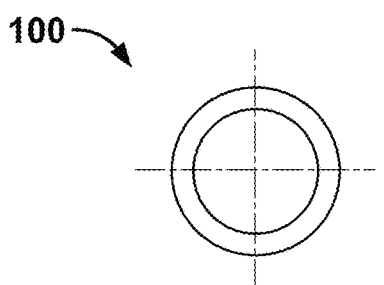

FIG. 6 shows another embodiment of a fixation rod 100. In an embodiment, fixation rod 100 includes a rod region 124 that may generally have the same diameter across its length and beveled or angled ends 127 that decrease into a smaller diameter. In an example, the constant diameter rod of FIG. 6 may be curved or include bends as described herein, see FIGS. 10-12. Similar to the above embodiments, each rod region 124 and beveled end 127 can be cylindrical in shape. The rod region 124 may have a substantially constant diameter D1, D2, D3 such as those described above and the beveled end may have a decreasing diameter. The decreasing diameter may be similar to the tapering of transition region T1 shown in FIG. 4, but may be less gradual and over a smaller length, in an example, see FIG. 6. In an embodiment, the decreasing diameter may occur over a length of 60 mm to 600 mm, in an example. It is noted that other starting and ending diameters and lengths of the transition region are also contemplated herein and form part of the disclosure. The values may be modified, for example, based on a patient's individual anatomy to provide custom morphology and desired rigidity or flexibility as described herein. The fixation rod 100 may be of any diameter as desired, including, in an example, 4.75 mm, 5.0 mm, 5.5 mm, 6.0 mm, and the like. The fixation rod 100 may be comprised of any material as desired including cobalt-chromium and titanium alloys, in an example.

Figure 7:
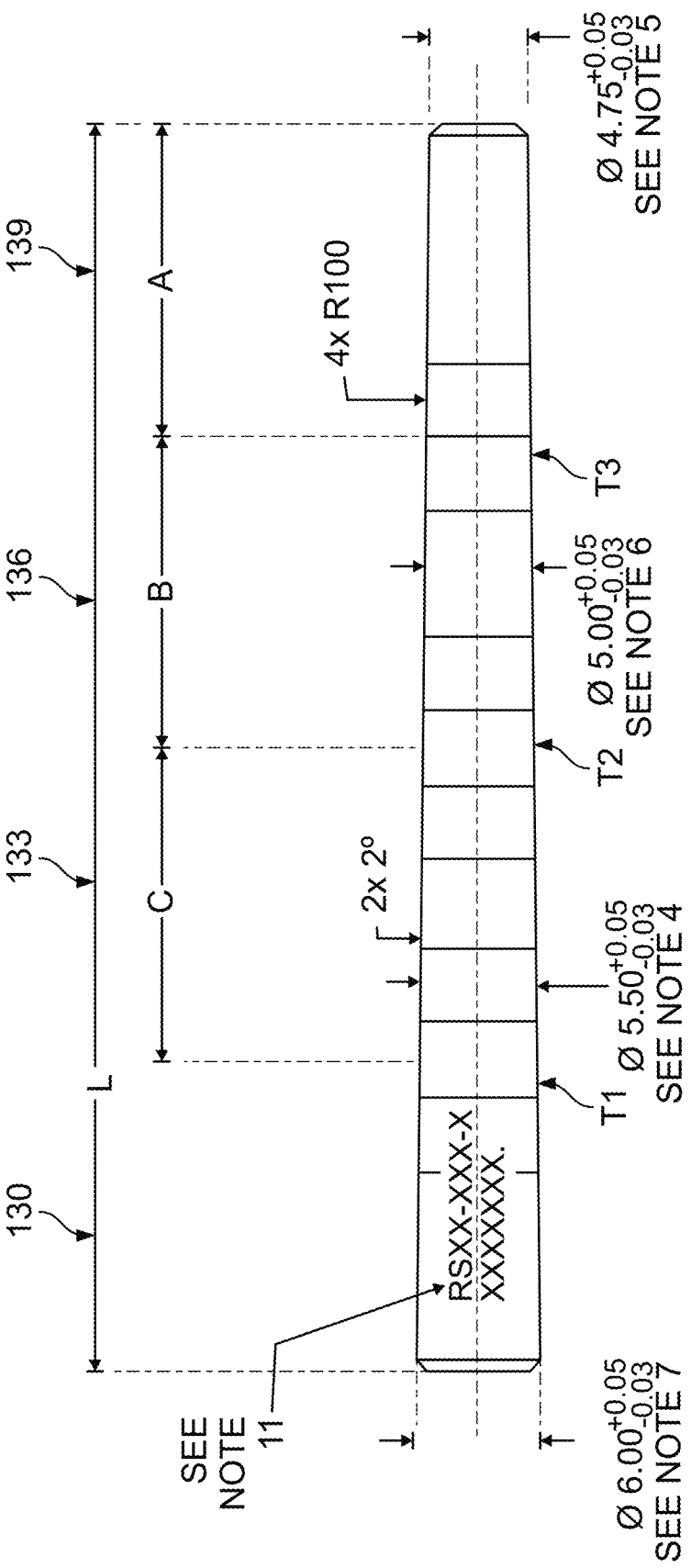
FIG. 7 is a side view of an embodiment of a fixation rod having a tapered diameter in accordance with various disclosed aspects herein.

FIG. 7 shows another embodiment of the fixation rod 100 that includes four rod regions 130, 133, 136, 139. The fixation rod in FIG. 7 may be generally similar to the fixation rod shown in FIG. 3, except that the length of the transition regions and linear regions may be variable and the amount of transition regions and linear regions may also be variable.

Moreover, fixation rod 100 may have no discrete defined zones (of constant and tapered sections) and unlimited transition zone placements to control in situ flex. In an example, the variable diameter rod including linear segments and tapered segments of FIG. 7 may be curved or include bends as described herein, see FIGS. 13A-E. As shown by FIG. 7, fixation rod 100 may be similar to fixation rod 10—it should also be noted that fixation rod 10, 100 may be referred to as a spinal rod. It is noted that all embodiments and description pertaining to fixation rod 10 may be similarly applied to fixation rod 100 unless context or this disclosure suggests otherwise. Similar to the above embodiments, each rod region 130, 133, 136, 139 can be cylindrical in shape with a substantially constant diameter D1, D2, D3 such as those described above. Transition regions T1, T2, T3 may separate the rod regions 130, 133, 136, 139 from each other and decrease the diameter from rod regions 130 to 133, 133, to 136, 136 to 139 in an example. The difference in diameter between rod regions 130, 133, 136, 139 may be subtle similar to rod regions 32, 34, 36.

The rate at which the diameter changes between diameters can optionally be constant across the length of the transition region T1, T2, T3. Thus, as shown in FIG. 7, the transition region T1, T2, T3 may form a substantially frusto-conical shape between the rod regions 130, 133, 136, 139. The transition region T1, T2, T3 may afford surgeons the flexibility to install the pedicle assemblies 12 at any location along the length of the fixation rod 100, including along the transition region T1, T2, T3 or at an intersection of the transition region T1, T2, T3 and one of the rod regions 130, 133, 136, 139. FIG. 9 shows additional embodiments including rod regions 150, 153, 156, 159 having different (but constant, in an embodiment) diameters and including transition regions T1, T2, T3 therebetween each successive region that transitions from the diameter of one region (e.g. 150) to the diameter of the next successive region (e.g. 153).

In an embodiment, the described systems and rods (e.g., including linear segments and gradual taper transitions) can be used in cervical and lumbar applications. The rods (e.g., including Bezier curves or a curved structure) may assist in anterior bending and rotation properly softening transitions between segments of the rod. It is noted that the described systems and rods may have linear segments and gradual taper transitions or Bezier curves or a curved structure (e.g., on a constant diameter rod) or both (e.g., Bezier curves or a curved structure on a variable diameter rod having linear segments and gradual taper transitions). It is noted that the number, length, position, and diameter of the linear segments (e.g., constant diameter segments) and the number, length, position, diameter, and slope, of the tapered segments (e.g., variable diameter segments) may be modified based on desired flex and rigidity, patient morphologies and anatomies, and other considerations such as those that may be evident during pre-operatively or intraoperatively. In an example, when the constant diameter segments are lengthened, the segments may have more flexibility and when the constant diameter segments are shortened, the segments may have more rigidity. Such modification of the length of the linear segments can be offset by the length of the curved regions, the tapered segments, or the Bezier curve transition regions, etc. In an example, a constant diameter segment of one diameter could be swapped or modified to a constant diameter segment having another, different diameter. The full control of the rod can tailored into infinite biomechanical solutions.

Figure 8:
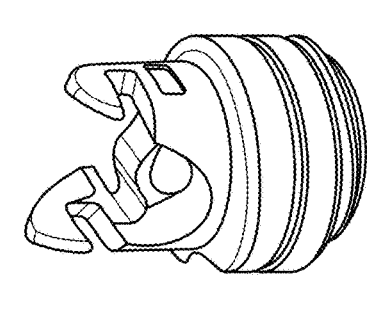
FIG. 8 shows various views of an embodiment of a fastener including a cap and screw in accordance with various disclosed aspects herein.
Figure 8:
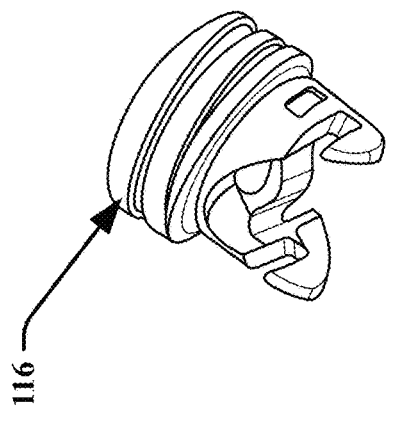
Figure 8:
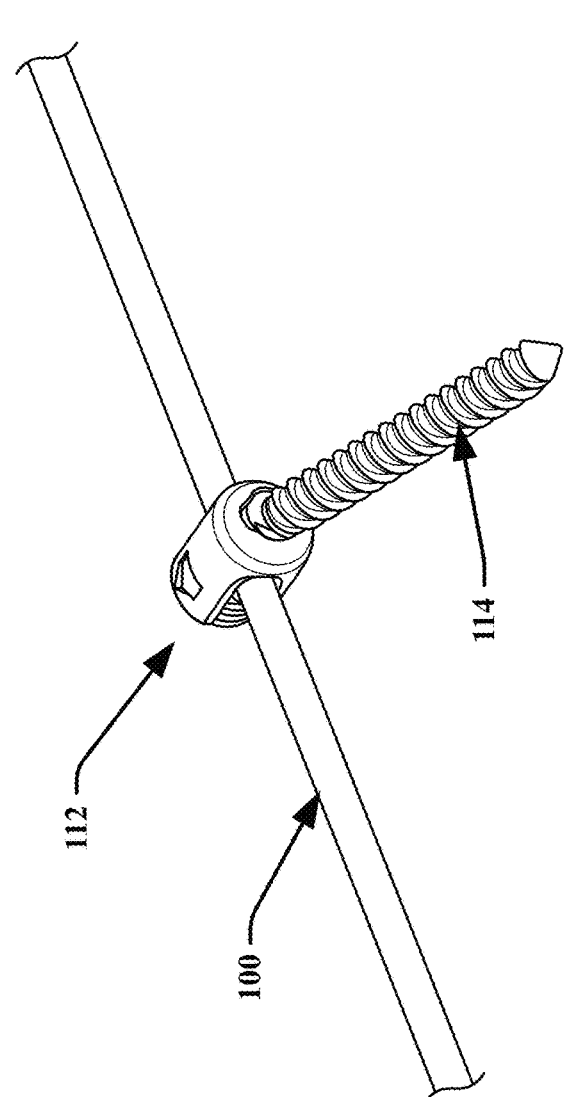
Figure 8:
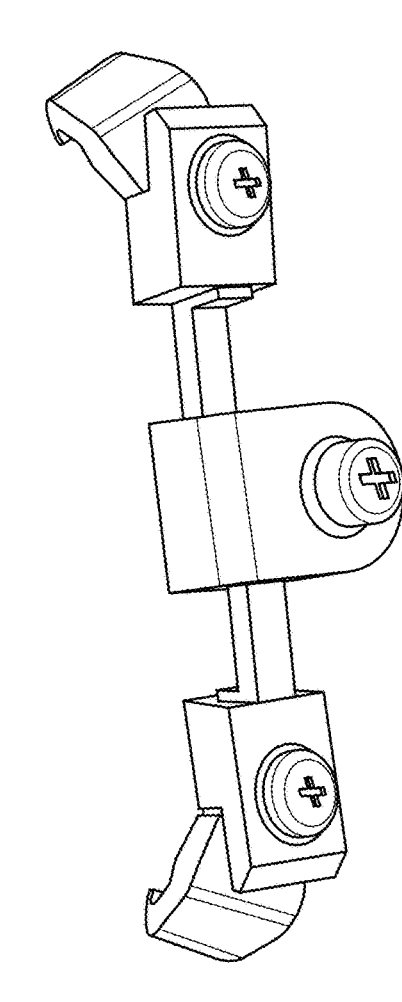

FIG. 8 shows an embodiment of a fastener 112 that can be used with the fixation rods described herein. The fastener may include a cap 116 and a screw 114. It is noted that the rod regions may be of any diameter. In an embodiment, two or more rod regions having different diameters (e.g., 130, 133, 136) (or regardless of diameter) can be placed in a single fastener 112 secured by one cap 116 and one screw 114. In an embodiment, the fastener may include a single screw tulip head secured by one locking cap. For example, three rod regions having different diameters 130, 133, 136 can be placed in a single fastener 112 secured by one cap 116 and one screw 114. For example three or more rod regions having different diameters 130, 133, 136 can be placed in a single fastener 112, e.g., secured by one cap 116 and one screw 114. One or more (or all) of the following may allow for multiple rod regions having different diameters to be placed in a single fastener 112 secured by one cap 116 and one screw 114, including the smooth transitions, the winged locking cap, the standard locking cap, the screw saddle design, and the tulip design. In an embodiment, the fastener and rod combination can allow for reduction in screw neck strain, contact, pressure, and/or stress shielding.

As described herein, the fixation rods 100 having varying diameters along discrete linear segments with smooth transition regions enables greater control over rod and screw placement, allowing the screws to accommodate the geometry of the patient's spine and not the rod design. Moreover, screw planning can be carried out preoperatively to predict rod bend. This can predict the performance of the rod based on the flex of the rod in various forms by the understanding the functionality and flex of the rod under different conditions from the lengthening or shortening of the fixed linear segments and the lengthening or shortening of the Bezier curve transitions. For example, an algorithm may be used to determine rod bend and screw placement to predict curvature. For example, the algorithm can calculate the location of the screws and additional parameters, such as pelvic incidence and sagittal balance, to predict a curvature, desired flexibility and rigidity, and/or the amount of correction needed to create a normal alignment. The algorithm can then calculate the curvatures and/or the amount of each linear and transition segment in terms of length and the flex (e.g., diameter) along with the Bezier curve transition regions if applicable to predict a flex in the rod and the amount of unloading (force) based on that bend and customized solution to predict the load or adjacent segment failure which can tie into the ligament and musculature and the negating of the construct stiffness. For example, the unloading of forces at adjacent segments may be used to predict the likelihood of PJK or adjacent segment failure, which may in turn relate to ligament and muscle performance as well as natural kyphotic events from natural aging, etc. In an embodiment, the algorithm may use a reference set. In an embodiment, the algorithm may provide calculations of the 3-D curvature, transition regions, linear regions, diameters, screw placement, and the like to provide precise sagittal alignment and coronal correction based on the in-situ functioning of the spinal rod. For example, the algorithm may be used to analyze the amount of correction and stresses that are inputted by the user or determined by the algorithm and how to use various patient parameters to determine and create precise 3-D curvature, transition regions, linear regions, diameters, screw placement, and reduction of construct stress.

Figure 9A:
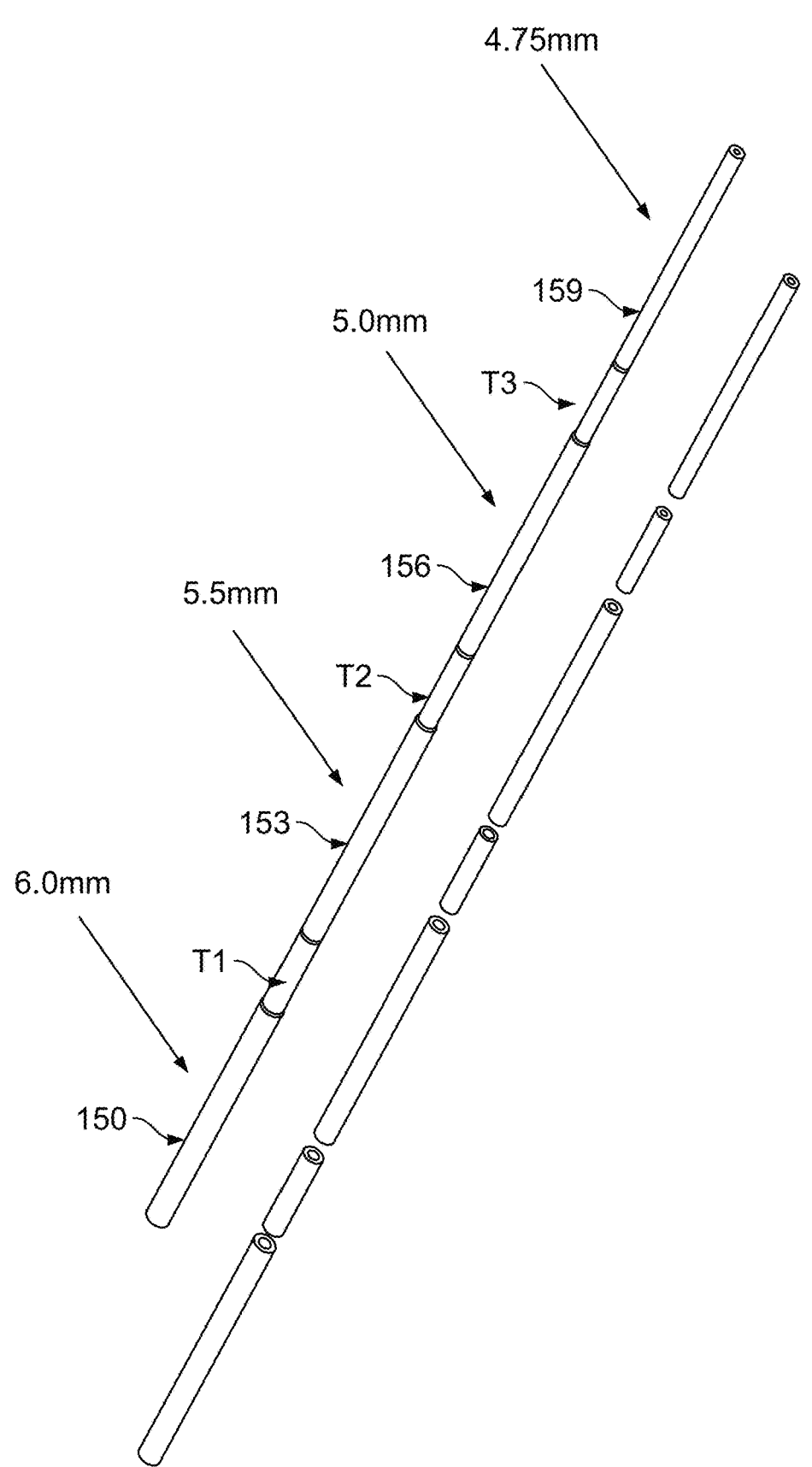
FIG. 9A shows exploded and assembled view of an embodiment of a fixation rod including one or more segments in accordance with various disclosed aspects herein.
Figure 9B:
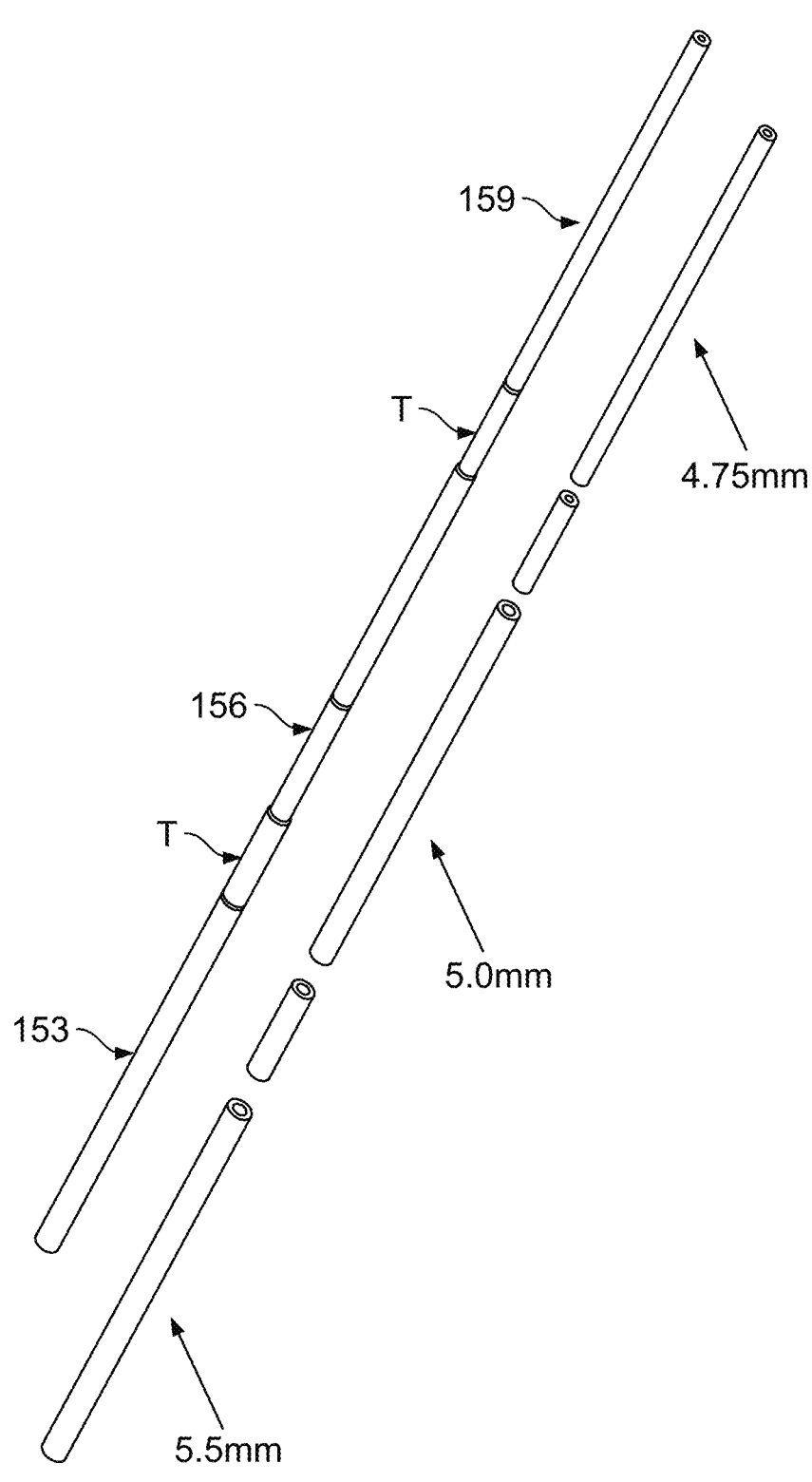
FIG. 9B shows exploded and assembled view of an embodiment of a fixation rod including one or more segments in accordance with various disclosed aspects herein.

In an embodiment, the fixation rod 100 may have a generally straight structure, see FIGS. 9A-B, for example. In an example, the variable diameter rod including linear segments and tapered segments of FIGS. 9A-B may be curved or include bends as described herein, see FIGS.

13A-E. In an embodiment, the fixation rod 100 may have a generally curved structure, see FIG. 12 and FIGS. 13A-E, for example. Generally, the curved structures or portions may be along the rod in either or both the linear segments and/or the transition segments. For example, the curved structures or portions may be positioned only in one or more linear segments, only in one or more transition segments, in both one or more linear segments and one or more transition segments but generally contained to an individual segment and terminating before the next adjacent segment(s), or in both one or more linear segments and one or more transition segments but generally extending through adjacent segments of linear and transition segments (e.g., the same curve extending through multiple segments). In an embodiment, the curved structures or portions may be placed within a linear segment or between linear segments.

In an embodiment, the curved structure may be a Bezier curve. For example, the curved structure can include a $2^{nd}$, $3^{rd}$, or $4^{th}$ order Bezier curve (defined by the order of smoothness in the curves and transitions), or other curved structure. It is noted that higher order Bezier curves may also be used. For the purposes of this disclosure, a Bezier curve may be generally understood, in an embodiment, as a parametric curve where a set of discrete "control points" defining a smooth, continuous curve by means of a formula. Usually the curve is intended to approximate a shape that otherwise has no mathematical representation or whose representation is unknown or too complicated. As described, the fixation rod 100 may include varying diameters along discrete linear segments with smooth transition regions. The varying diameters and smooth transition regions between varying diameters can be used to mimic the anatomical variation in stiffness of the proximal vertebral column to assist mitigation of PJK and implant failure due to stress shielding, for example. The fixation rod 100 can provide full control over the length of transition regions, as well as the length and diameters of linear segments, to tune local rod stiffness. The transition regions, or larger rod, may further include Bezier surface geometry or a curved structure, which can also eliminate the stress concentrations found in stepped rods, and extend implant life. As described, artificial intelligence may be used to provide curvature morphotypes and corrective fixation tuned to individual patients' anatomies and provides assistance in predicting adjacent segment disease at subsequent levels.

Figure 10:
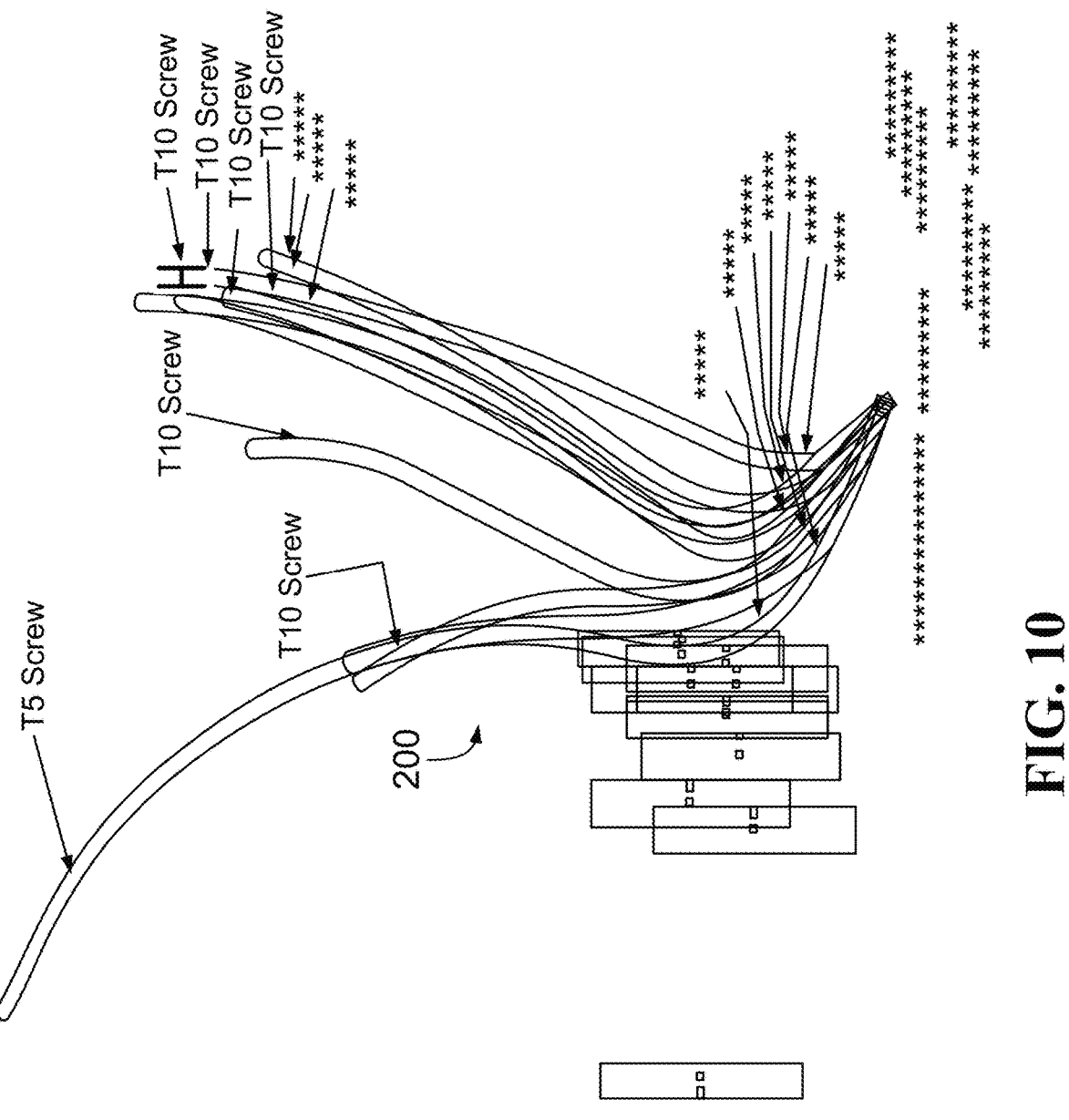
FIG. 10 shows a condensed distillation of fixation rod morphologies in accordance with various disclosed aspects herein.
Figure 11:
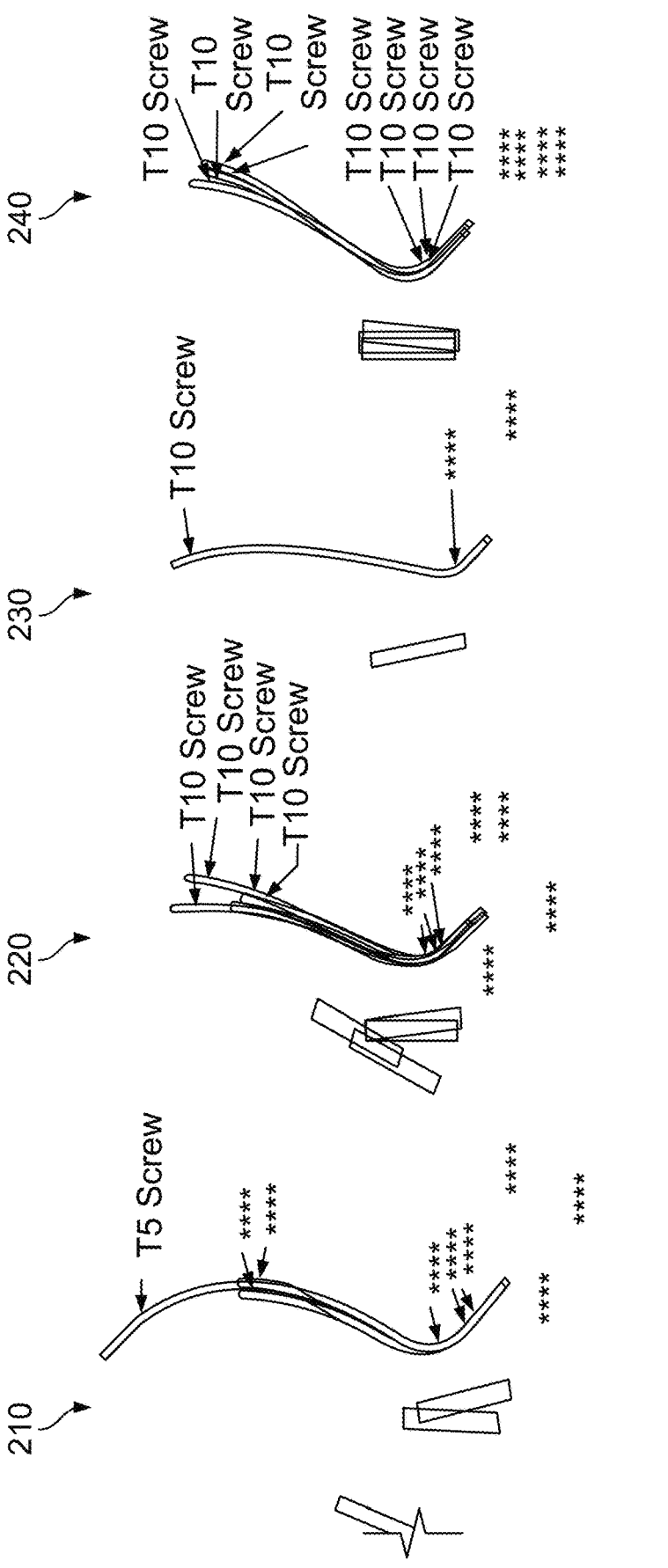
FIG. 11 shows the condensed distillation of fixation rod morphologies of FIG. 10 separated into sets in accordance with various disclosed aspects herein.
Figure 12:
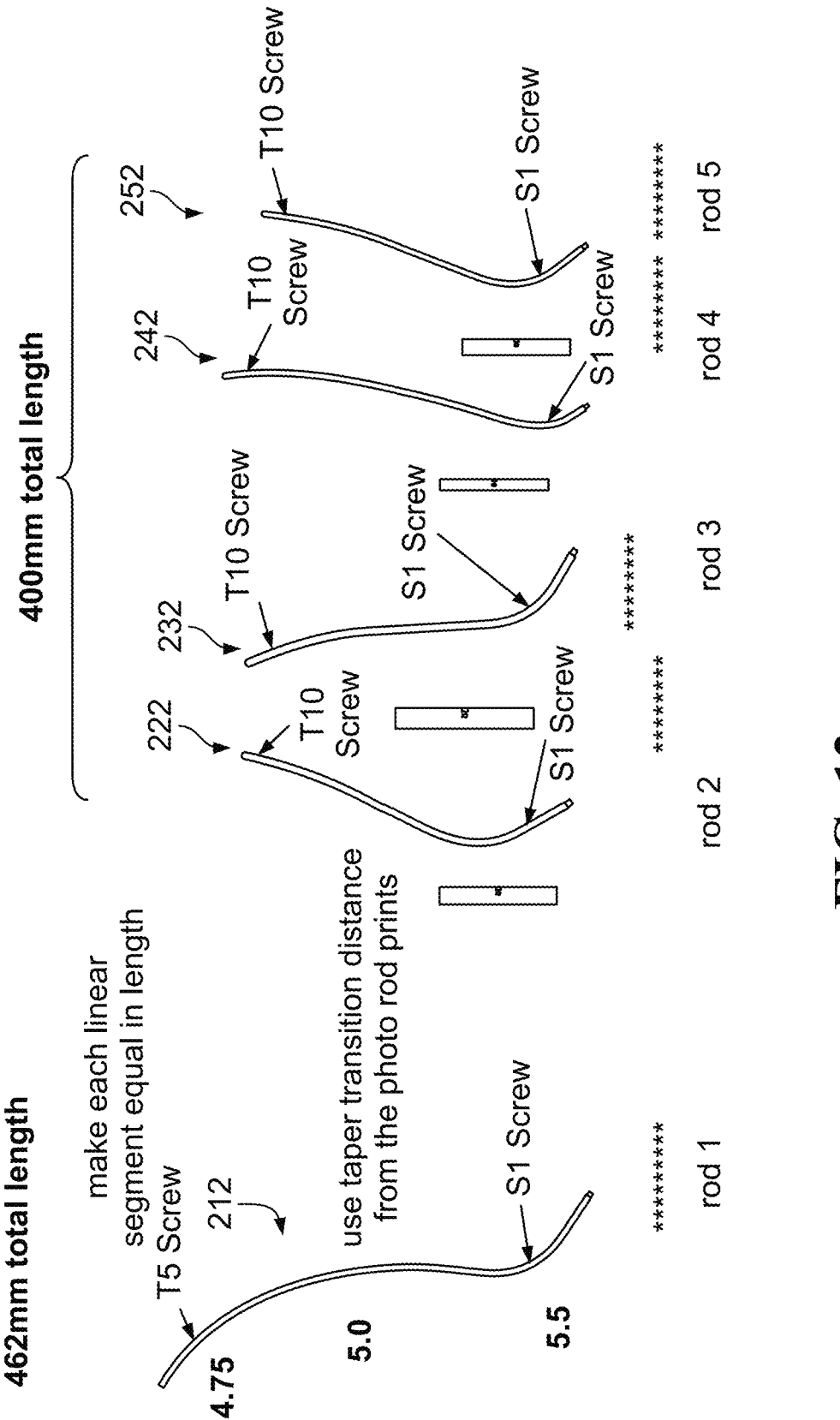
FIG. 12 shows embodiments of fixation rods based on the sets of condensed distillation of fixation rod morphologies of FIG. 11 in accordance with various disclosed aspects herein.
Figure 13A:
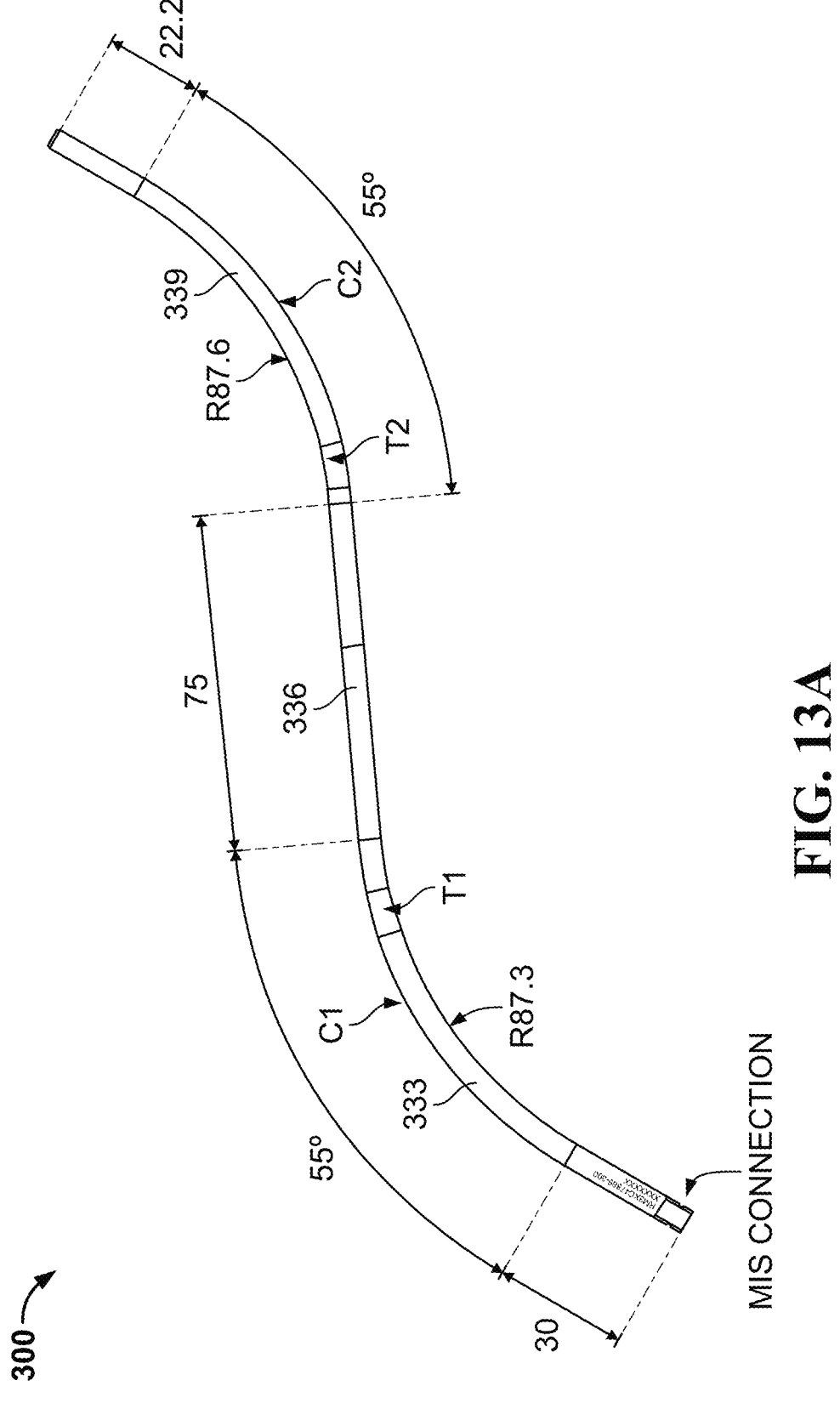
FIGS. 13A-E show embodiments of fixation rods including one or more segments and curved morphologies in accordance with various disclosed aspects herein.
Figure 13B:
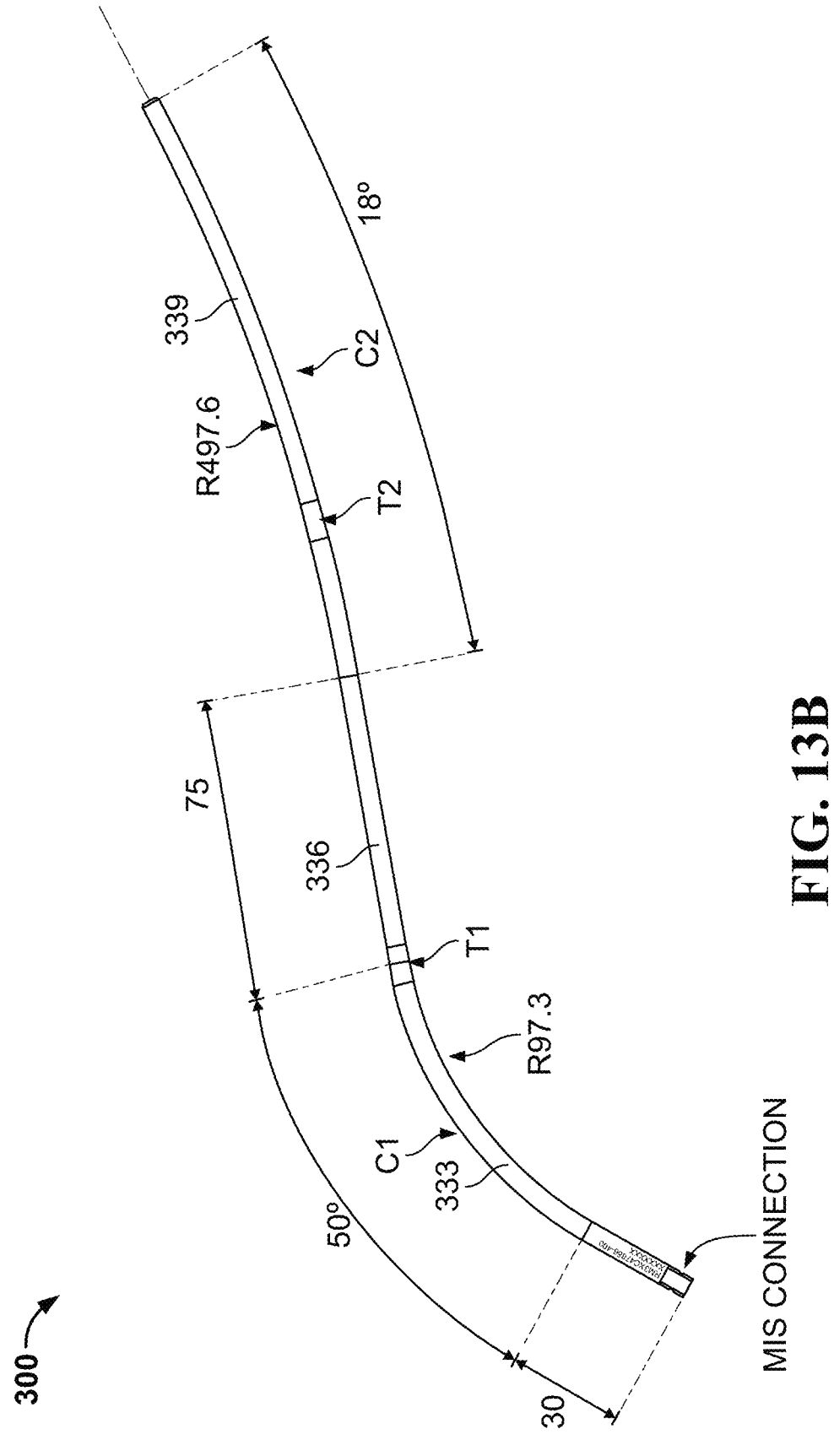
Figure 13C:
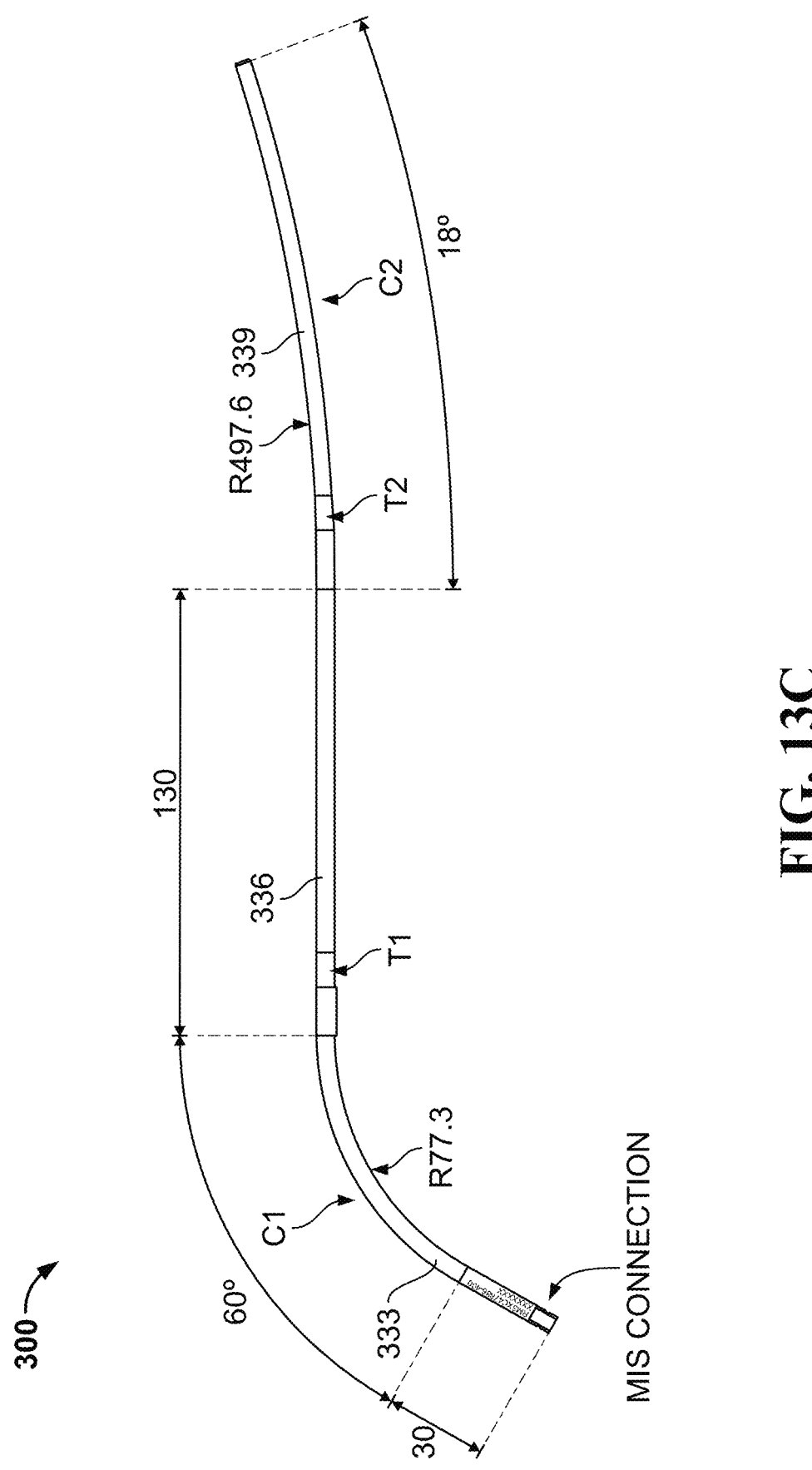
Figure 13D:
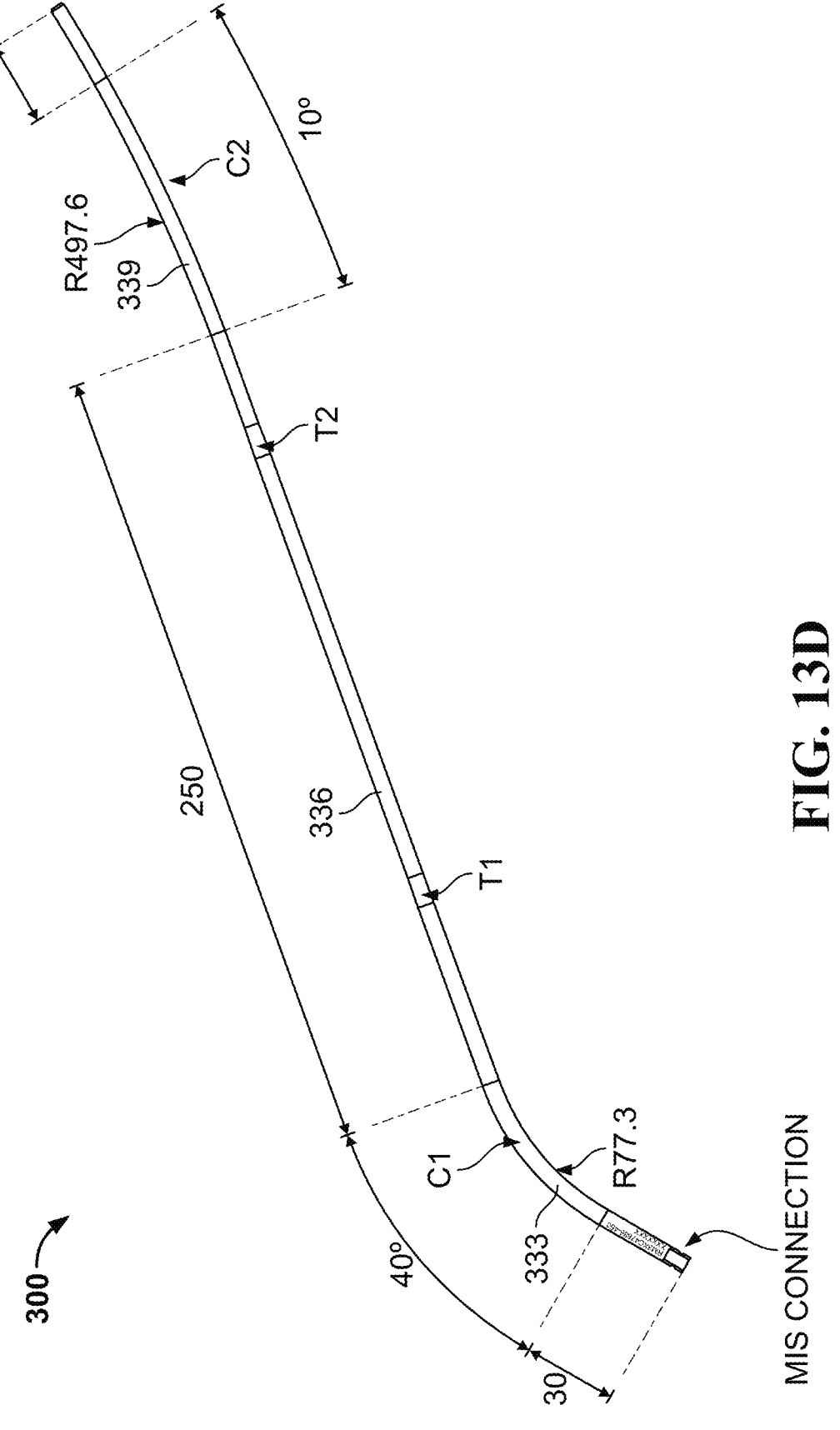
Figure 13E:
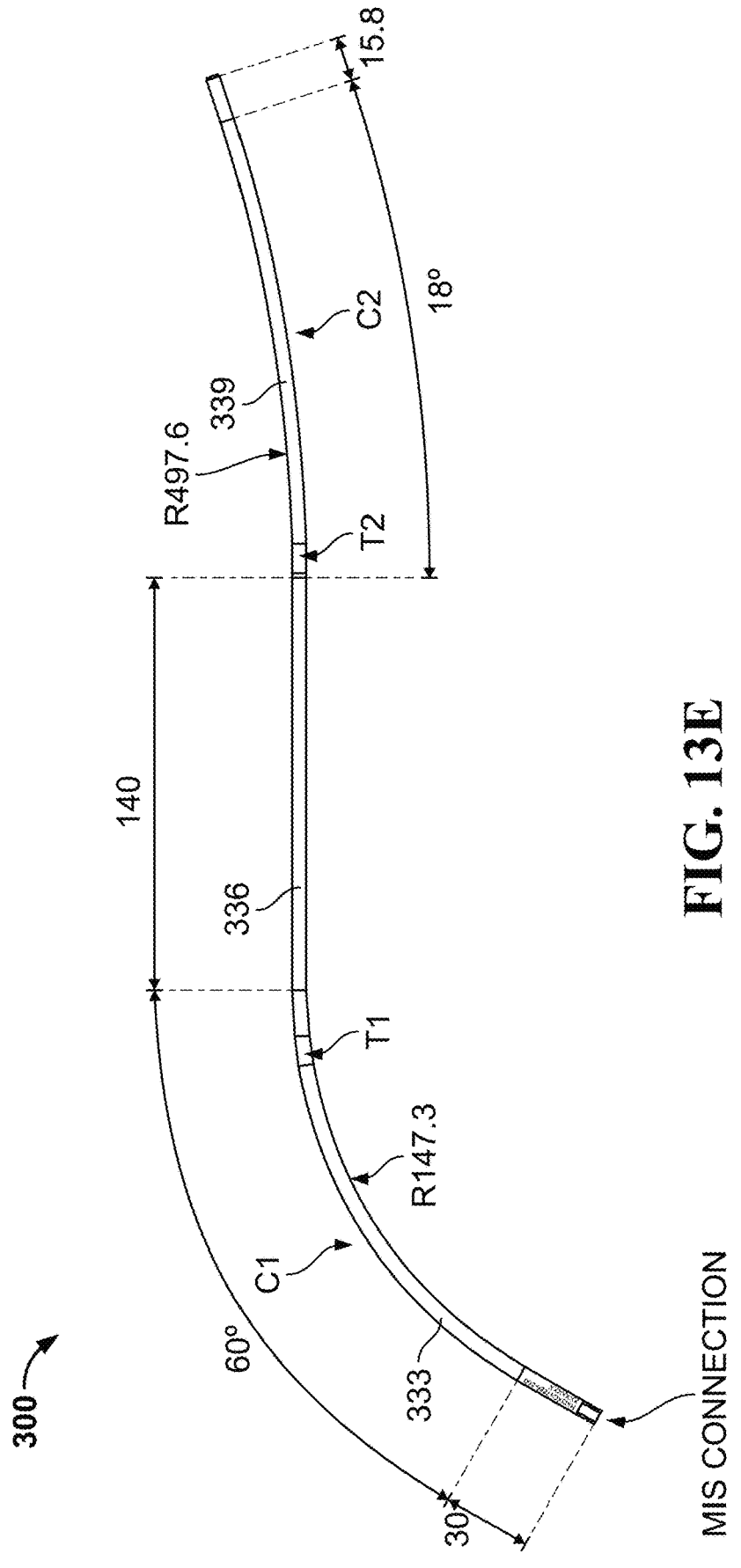

FIGS. 10-12 show various fixation rod morphotypes 212, 222, 232, 242, 252. The fixation rod morphotypes 212, 222, 232, 242, 252, may have a constant diameter along the length of the fixation rod (e.g., similar to FIG. 6A-C) as well as a shape and curvature that mimics and is adaptable to a patient's unique morphology as described herein. Alternatively, the fixation rod morphotypes 212, 222, 232, 242, 252, may have constant diameter rod regions as well as the transition or tapered regions described herein (e.g., similar to FIGS. 7 and 9A-B) as well as a shape and curvature that mimics and is adaptable to a patient's unique morphology as described herein, see FIGS. 13A-E. Generally, the curvatures may be placed anywhere on the fixation rod as desired, relative the constant diameter regions (e.g., linear segments) and the transition regions (e.g., transition or tapered segments). Placement of the curvatures may be generally based on a patient's anatomy and the desired health outcome. For example, the desired curvature may be dependent on individual surgical cases and anatomies. In an embodiment, curvatures may be positioned above or below junctions such as the thoracolumbar junction or cervical thoracic of where biomechanics or correction takes place, in an example, to strategically control the forces to reduce overall construct stiffness. In an embodiment, desirable fixation rod morphotypes (e.g., 212, 222, 232, 242, 252) may be generated using artificial intelligence.

FIGS. 13A-E show various fixation rods 300 having constant diameter segments (also referred to as linear segments herein) 333, 336, 339, tapered segments or Bezier curve transition regions T1, T2, and curvatures C1, C2. Regions T1, T2 may be between the linear segments or in the linear segments 333, 336, 339. As described, the fixation rods 300, may have constant diameter rod regions as well as the transition or tapered regions described herein (e.g., similar to FIGS. 7 and 9A-B) as well as a shape and curvature that mimics and is adaptable to a patient's unique morphology as described herein. Alternatively, the fixation rods 300, may have a constant diameter along the length of the fixation rod (e.g., similar to FIG. 6A-C) as well as a shape and curvature that mimics and is adaptable to a patient's unique morphology as described herein, see FIGS. 10-12. Generally, the curvatures may be placed anywhere on the fixation rod as desired, relative the constant diameter regions (e.g., linear segments) and the transition regions (e.g., transition or tapered segments). The curvature of the shape of the rod can vary. In an example, to go in the opposite direction may be rare due to removing lordosis in the lumbar spine. In an example, kyphotic curves can go negative to straighten out the patient as well as sagittal and coronal curves related to the morphotype rods or patient specific rods. Placement of the curvatures may be generally based on a patient's anatomy and the desired health outcome. For example, the desired curvature may be dependent on individual surgical cases and anatomies. In an embodiment, curvatures may be positioned above or below junctions such as the thoracolumbar junction or cervical thoracic of where biomechanics or correction takes place, in an example, to strategically control the forces to reduce overall construct stiffness. In an embodiment, desirable fixation rod curves may be based on morphotypes (e.g., morphotypes 1, 2, 3, 4, and 5 shown in FIG. 12) and may be generated using artificial intelligence.

Figure 14:
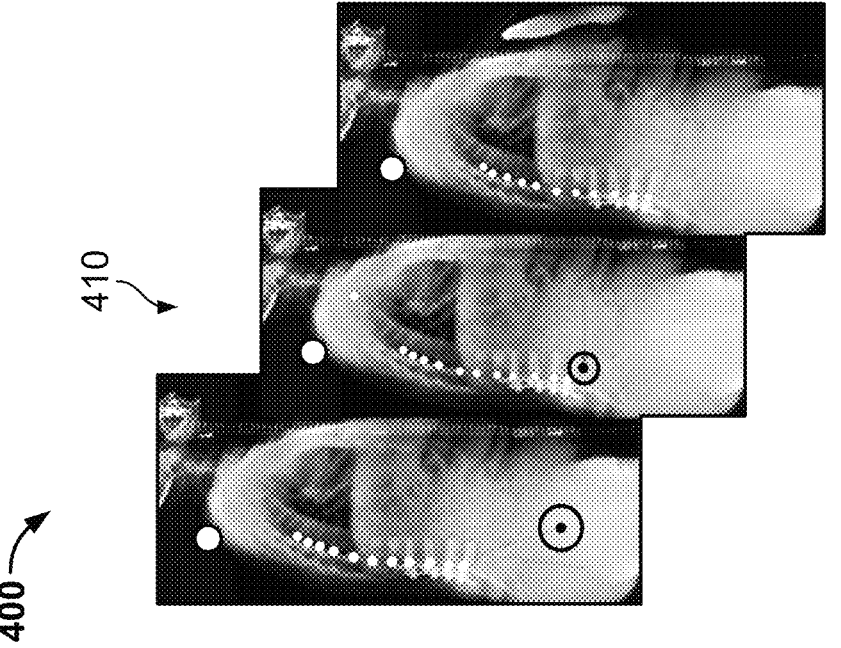
FIG. 14 shows embodiments of a fixation rod as placed in a patient and method steps used to determine and provide a fixation rod customized to the patient's morphology in accordance with various disclosed aspects herein.
Figure 14:
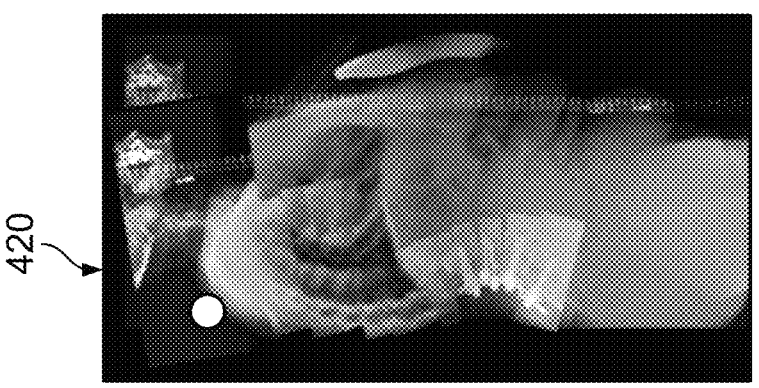
Figure 14:
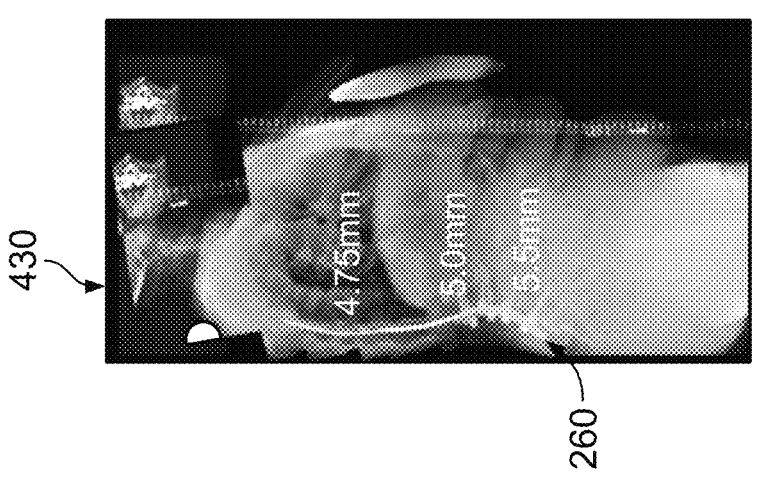

Method 400 shown in FIG. 14 may include step 410 surgical planning, step 420 osteotomy simulation, and step 430 AI-optimized patient specific multi-diameter fixation rods, to generate a custom multi-diameter fixation rod 260. The custom multi-diameter fixation rod 260 may include a curvature and bends that reflect curvatures and bends from post operative results and pre-planning measurements that reflect spinal curvatures in transition rods and constant diameter rods. The number, length, diameter or slope, degree, and position of the curves may be variable and may be generally based on the desired shape, flexibility, and rigidness of the spinal rods and the amount of correction needed for the patient. As described herein, desired shape, flexibility, and rigidness of the spinal rods and the amount of correction needed for the patient may also determine the number, length, diameter or slope, and position of the constant diameter segments and the variable diameter segments. It is noted that the curves may be defined or determined by the degree (e.g., standard curves extending through the x, y, and/or z planes), may be Bezier curves (e.g., curves having a more irregular or non-standard shape or having discrete "control points" that alter the arc of the curves), or may be curves based on combined morphologies (such as types 1, 2, 3, 4, or 5 shown in FIG. 12). It is noted that any of the foregoing curves (standard, Bezier, morphological, and others) may have a constant diameter (e.g., FIG. 12) or a variable diameter (e.g., FIGS. 13A-E). In regard to FIG. 13A-E, the transition segments having a variable diameter and leading into, preceding, or within a Bezier curve may also be referred to as Bezier curve transition regions as described herein.

For example, FIG. 10 shows a condensed distillation of fixation rod morphologies 200 from 700 post operative results. These condensed distillation of fixation rod morphologies 200 may be separated into sets, such as sets 210, 220, 230, 240 shown in FIG. 11. The sets 210, 220, 230, 240 may then be used to provide one or more fixation rod morphotypes 212, 222, 232, 242, 252, see FIG. 12. The morphotypes shown in FIGS. 10-13 may be patient matched so that the bends or curves of the fixation rod may be customized to a specific patient's anatomy. The pre-determined bends or bends in-situ combined with the tapered transition segments may allow for the desired bend, flex, and unloading of the forces to be predicted in-situ and create a biomechanically beneficial solution. The tapered transition segments, when placed at the apex of a curve, for example, can allow for the bend to be smooth and not notched, stepped, or kinked. In an embodiment, the Bezier curve transition regions may allow the transition between the constant segments (e.g., as a tapered or transition segment). The Bezier curve transition regions may also allow for the Bezier curve transition regions to be placed leading into, preceding, or within a constant diameter segment. The Bezier curve transition region can be located anywhere in a bend (standard, Bezier, or morphotype bend) and even on a straight or standard curved rod. By having these Bezier curve transition regions, the rod may have improved or controlled flex and may be bent or curved and smooth without kinks in the rod or interference by steps etc.

These one or more fixation rod morphotypes 212, 222, 232, 242, 252 may generally include a curvature that is similar to actual morphotypes exhibited by patients so that the fixation rod morphotypes may provide better adaptability to patients and better outcomes. Additionally, the rod morphotypes and methods of generating the rod morphotypes thereof may allow insertion of a rod from occiput to sacrum with the single rod (e.g., one rod having different diameters and tapers or transition regions in one rod) in two screw platforms, a poster cervical platform and thoracolumbar platform. It is noted that the described rods and methods may also any number of screw platforms, including less than two or more than two (e.g., 1, 3, 4, 5, 6, 7, 8, 9, 10, etc. screw platforms), without departing from this disclosure. Generally, screws may get smaller towards the posterior cervical thus preventing use of a thoracolumbar spine platform for a cervical platform. The described rods and methods allow modification of the lumbar to work and function the same in the cervical so that a single rod and/or less screw platforms may be needed.

Moreover, the rod morphotypes and methods of generating the rod morphotypes thereof may enable the use of three or more different diameter segments using one single screw head with one locking cap. In an embodiment, four or more individual rod diameters may be used with one screw wherein the screw is placed in the pedicles of the vertebral bodies and the rod is placed in that screw's head which then has a locking cap laid on top of the rod in the screw head to attach the components together. The one or more fixation rod morphotypes 212, 222, 232, 242, 252 generated may be further customized to a specific patient to generate the custom multi-diameter fixation rod 260 for that patient, in an example. In an embodiment, the systems and methods may incorporate artificial intelligence to generate the one or more fixation rod morphotypes 212, 222, 232, 242, 252 and/or the custom multi-diameter fixation rod 260. In an embodiment, the systems and methods may use artificial intelligence to give in situ predictions on the unloading of adjacent segments. In an embodiment, an algorithm may be used that determines how the constructs unload in situ to give a prediction on adjacent segment strain, stress, and failure.

The system and methods may utilize predictors to generate the one or more fixation rod morphotypes 212, 222, 232, 242, 252 and/or the custom multi-diameter fixation rod 260. For example, the systems and methods may utilize predictors based upon the curves, bending, and loading and functions of rods based on biomechanics in-situ between the rod and the rod, cap, and screw interface. Additionally, the systems and methods may be able to provide failure predictors in-situ off cumulative of rod data pre and post operative by forming a data base allowing us to predictability (red, yellow, green light valuations, for example) based upon rod flex. The systems and methods may further incorporate predictions based on general rod implant performance. In an embodiment, the rods, and caps and screws may be used to address proximal junction kyphosis, proximal junction failure and adjacent segment disease. In an embodiment, the tailoring of the different diameter rods both in singular use and in the transition, rods help match the rod diameter to the bine quality to reduce micro motion, contact pressures and stress shielding, for example. Generally, the described rods herein may be used in degenerative spine, adult deformity, and pediatric applications, for example.

As applicable to all embodiments described herein, e.g., spinal rods having a constant diameter and curved, spinal rods having a variable diameter and straight, spinal rods having a variable diameter and curved, and wherein any of the foregoing curves are a result of morphologies (e.g., types 1, 2, 3, 4, or 5 shown in FIG. 12), the lengths of the spinal rods may range from about 60 mm to about 600 mm. For example, the lengths of the spinal rods may be about 60, 70, 80, 90, 100, 150, 200, 250, 300, 350, 400, 450, 500, 550, and 600 mm, and the like, and any values therebetween. As applicable to all embodiments described herein having a constant diameter, e.g., spinal rods having a constant diameter and curved, and wherein any of the foregoing curves are a result of morphologies (e.g., types 1, 2, 3, 4, or 5 shown in FIG. 12), the constant diameter of the spinal rods may range from about 4.75 to 6.0 mm. For example, the constant diameter of the spinal rods may be about 4.75, 5.0, 5.25, 5.5, 5.75, and 6.0 mm, and the like, and any values therebetween. As applicable to all embodiments described herein having a variable diameter, e.g., spinal rods having a variable diameter and straight, spinal rods having a variable diameter and curved, and wherein any of the foregoing curves are a result of morphologies (e.g., types 1, 2, 3, 4, or 5 shown in FIG. 12), the variable diameter of the spinal rods may range from about 4.75 to 6.0 mm. For example, the variable diameter of the spinal rods may be about 4.75 to 6.0 mm, 4.75-5.5 mm, and the like, and any ranges of values therebetween. For example, the variable diameter of the spinal rods may decrease by approximately 0.1 mm per transition segment, 0.25 mm per transition segment, 0.5 mm per transition segment, 0.75 mm per transition segment, 1.0 mm per transition segment, and the like.

Each transition segment may have the same decreasing or increasing values (e.g., decreasing by 0.1 mm the preceding linear segment), may have the same slope or a generally constant slope (e.g., decreasing or increasing by no more than 0.05 mm from the preceding linear segment over ×mm length), or may have different decreasing and increasing values (e.g., one transition segment decreasing by 0.1 mm the preceding linear segment and another transition segment decreasing by 0.25 mm the preceding linear segment), or different slopes (e.g., one transition segment decreasing by 0.1 mm the preceding linear segment over ×mm length and another transition segment decreasing by 0.1 mm over 2×mm length; also one transition segment decreasing by 0.1 mm the preceding linear segment over ×mm length and another transition segment decreasing by 0.25 mm over ×mm length; also one transition segment decreasing by 0.1 mm the preceding linear segment over ×mm length and another transition segment decreasing by 0.25 mm over 2×mm length; and the like). All transition segments may decrease in diameter in succession in the same spinal rod, all transition segments may increase in diameter in succession in the same spinal rod, or some transition segments may increase in diameter while others decrease in diameter in the same spinal rod. In an embodiment, outer or end diameters may be the same value, while inner diameters may be variable, thereby comprising tapered sections that decrease and increase a same net amount along the length of the spinal rods. In an embodiment, outer or end diameters may be different values (e.g., smaller or larger than one another), thereby comprising tapered sections that decrease and/or increase a different net amount along the length of the spinal rods. In an embodiment, one or both of the outer or end segments of the spinal rods may be constant diameter segments, variable diameter segments, curved, Bezier curved, morphologically curved, or straight. In an embodiment, tapered segments may be placed between or in constant diameter segments to control a kick point.

As applicable to all embodiments described herein having a curved structure, the spinal rods may include any number or curves, including 1, 2, 3, 4, 5, 6, 7, 8, 9, 10, etc. curves. The curves may be in a direction, e.g., in the x, y, and/or z plane. The curves may be Bezier curves regular curves, or irregular curves. The curves may be located on any portion of the spinal rods, including at the ends, not at the ends, in the interior sections, on the transition segments (if any), on the constant (or linear) diameter segments, and the like. The curves may start and terminate in the same segment, e.g., a transition segment or a constant diameter segment, or the curves may extend over multiple segments, e.g., one transition segment and one constant diameter segment, two transition segments and one constant diameter segments, one transition segment and two constant diameter segments, one or more transition segments and one or more constant diameter segments, at least one transition segment and at least one constant diameter segment, two or more transition segments, two or more constant diameter segments, at least two transition segments, at least two constant diameter segments, and the like. The curves may start and terminate at any point on the transition segments and/or a constant diameter segments so that the curves may include the entire segments or may include a only portion of the segments. In an embodiment, the curves may be about 1° to >90° (from the reference of the start or one end of the curve, noting that if the curve changes direction, this would comprise a new or second curve for the purposes of this disclosure). In an embodiment, the curves may be about 5° to about 70°, 10° to about 60°, and the like, including any ranges therebetween.

It is noted that other ranges and values of the foregoing are also herein contemplated and form a part of this disclosure. It is noted that for any range described herein in this disclosure, the terms approximately or about are understood to include±10% the described value.

In an embodiment, the described systems and methods may be utilized to provide partial or shorter spinal rods. For example, the described morphotypes may be split into smaller rods depending on the desired placement and outcomes. The described rods can be adapted to address just the kyphotic segment or the lower lumbar segment by claiming by utilizing pelvic parameters or sacral parameters to reduce adjacent segment even with a constant diameter rod. In an embodiment, the described systems and methods may use Cobb angles, Proper Pelvic Incidence rod contouring in the Bezier curved platform or stepped, constant, or conical rod platforms and the assistance of reducing segmental lordosis In an embodiment, the flex of the described rods may be controlled and adapted based on manipulation of the linear segments or the transitions regardless of the diameter of the linear segment, length of the segment, or the length of the taper. In an embodiment, the flex of the described rods may be controlled and adapted based on manipulation of the added curvatures of the described rods regardless of the diameter of the linear segments, length of the segments, or the length of the taper. In an embodiment, biomechanics may be accounted for through the rod cap and screw interface. In an embodiment, biomechanics may be accounted for through a biomechanical transition. For example, the biomechanical transition can enable transition from one segment to another segment (e.g., linear and tapered segments) or to effectuate desired curvature of the rods. The biomechanical transition can include a dampener, biasing member, and spring coil. The biomechanical transition can be used to provide a desired curve or shape of the rod, for example, based on the anatomy of a patient during surgery, and may then hold or retain the curve permanently. The biomechanical transition or spring may be placed anywhere on the rods where there is a need or desire for flex or transition to soften the construct. For example, the biomechanical transition or spring may be placed anywhere along a linear segment, tapered segment or transition regions to add a curve or flex or to form a Bezier curve transition region or morphotype curve region (e.g., types 1, 2, 3, 4, or 5 shown in FIG. 12). In an example, a biomechanical transition may be placed on a linear segment or tapered segment to be able to modify those segments into a curve. The modification may be made during a patient consult, intraoperatively, or the like, to make a customized curvature of the rods to the patient's anatomy.

Generally, the described rods may provide one or more (or all) of the following: z-state benefits (e.g., rod can be turned to provide an anatomical match and spinal support in x, y, and z directions), intraoperative modifications (e.g., sizing larger rod down to a smaller size with desired taper and/or curvature; turning rod for z-direction adaptability; adding curves or tapered segments as desired on site), softer transitions of diameters, segments, and curves, softer proximal loading, reduction of forces unloading on the proximal junction, reduction of PJK based on how the rods are curved or shaped, reduction of micro-movement of the rods, biomechanical benefits to reduce construct stiffness, general flexibility and adaptability of the rods and a reduction of stiffness across the whole rod that is more akin to the human body, added compression between two segments, and the like.

The described rods may comprise different metals and different geometries for example around the apex of the rods. The different metals and different geometries may also enable different amounts of flex in the described rods. Non-limiting examples of different materials that may be used include, titanium, aluminum, cobalt chrome or cobalt chromium, peek, carbon fiber, molybedenum-rhenium, a combination of two or more thereof, and the like. It is noted that the material may be chosen or adapted to provide flexibility or rigidity. Different segments (linear and transition segments or portions of the curved and/or non-curved segments) may comprise different materials. In an embodiment, the materials of the described rods may contribute to the flexibility of the rods. Non-limiting examples of different geometries that may be used include oval hexagonal, oblong boxed, a combination or two or more thereof, and the like.

In an embodiment, the method of manufacture may comprise machining the spinal rod. In an embodiment, the spinal rod may be monolithically formed. In an embodiment, the spinal rod may be formed with tapered sections as desired or the spinal rod may be modified to have tapered sections as desired (e.g., by removing material, etc.). In an embodiment, the spinal rod may be formed with curves as desired or the spinal rod may be modified to have curves as desired (e.g., by bending with appropriate equipment, etc.).

In an embodiment, the generated and custom rod morphologies incorporate at least two different diameter segments having a tapered transitional segment therebetween. The systems and methods of generating the rod morphologies may be based off the bends of the rods and how the rods function between the rod and fastener (e.g. cap and screw) interface softening the transitions of the spinal segments and rod segments to be able to reduce PJK/PJF/adjacent segments disease.

It is noted that this disclosure describes spinal rods having linear and tapered sections (e.g., with a varying diameter along the length of the rod), spinal rods having curvatures (that have a constant diameter), and spinal rods having linear and tapered sections and curvatures (thereby also having a varying diameter along the length of the rod).

Illustrative embodiments have been described, hereinabove. It will be apparent to those skilled in the art that the above devices and methods may incorporate changes and modifications without departing from the general scope of this invention. It is intended to include all such modifications and alterations within the scope of the present invention. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A spinal rod, comprising:

at least two segments having a constant diameter, wherein a first segment has a first constant diameter and a second segment has a second constant diameter, and wherein the first constant diameter is different from the second constant diameter, and a transition region positioned between the at least two segments, wherein the transition region has a variable diameter that gradually transitions between the first constant diameter and the second constant diameter, wherein the transition region comprises a tapered shape around an entirety of a perimeter of the transition region; and at least one curve extending along the at least two segments, wherein a shape of the at least one curve and a length of each segment and the transition region is customizable to a specific patient anatomy.

2. The spinal rod of claim 1, wherein the at least two segments and the transition region are monolithically formed.

3. The spinal rod of claim 1, wherein the at least two segments and the transition region are devoid of a full, sharp step that forms a 90° angle relative to a longitudinal axis of the at least two segments and the transition region.

4. The spinal rod of claim 1, wherein the at least two segments and the transition region comprise a smooth surface across a full length thereof.

5. The spinal rod of claim 1, wherein the transition region gradually tapers from the first constant diameter of the first segment to the second constant diameter of the second segment.

6. The spinal rod of claim 1, wherein the transition region comprises a generally constant slope.

7. The spinal rod of claim 1, wherein the transition region is at least 5 mm in length.

8. The spinal rod of claim 1, wherein the at least one curve comprises a Bezier curve.

9. The spinal rod of claim 1, further comprising a third segment having a third constant diameter wherein the third constant diameter is different from the first and the second constant diameters and a second transition region between the second segment and the third segment.

10. The spinal rod of claim 1, wherein a shape of the at least one curve is determined by an algorithm that determine common sets of morphologies based on a database of patient data.

11. A fixation rod, comprising:

a first segment comprising a first constant diameter and a second segment comprising a second constant diameter, wherein the first constant diameter is different from the second constant diameter, and a transition region positioned between the first and second segments, wherein the transition region has a variable diameter that gradually transitions between the first constant diameter and the second constant diameter, wherein the transition region has a constant slope around an entirety of a perimeter of the transition region, a curve in at least one of the first segment, the second segment and the transition region, wherein the curve and a length of the first and second segments and the transition region is customizable to a specific patient anatomy.

12. The fixation rod of claim 11, wherein the curve is in the first segment, the second segment and the transition region.

13. The fixation rod of claim 11, wherein the first and second segments and the transition region are monolithically formed.

14. The fixation rod of claim 13 further comprising a longitudinal axis, wherein the first and second segments and the transition region are devoid of a step that forms a 90° angle relative to the longitudinal axis.

15. The fixation rod of claim 13, wherein the first and second segments and the transition region form a smooth surface across a full length thereof.

16. The fixation rod of claim 11, wherein the transition region gradually tapers from the first constant diameter of the first segment to the second constant diameter of the second segment.

17. The fixation rod of claim 11, wherein the curve comprises is a Bezier curve.

18. The fixation rod of claim 11, wherein a shape of the curve is determined by an algorithm that determines common sets of morphologies based on a database of patient data.

* * * * *